United States Patent
Mallams

Patent Number: 5,925,757
Date of Patent: Jul. 20, 1999

[54] METHOD FOR PREPARING CARBOXAMIDES

[75] Inventor: Alan K. Mallams, Hackettstown, N.J.

[73] Assignee: Schering Corporation, Kenilworth, N.J.

[21] Appl. No.: 08/912,625

[22] Filed: Jul. 23, 1997

Related U.S. Application Data

[60] Provisional application No. 60/021,009, Jul. 26, 1996, and provisional application No. 60/028,926, Sep. 13, 1996.

[51] Int. Cl.$^6$ .................. C07D 401/14; C07D 401/06
[52] U.S. Cl. ..................... 544/361; 544/360; 546/93; 546/189
[58] Field of Search ..................... 544/58.2, 361, 544/126, 360; 546/93, 189

[56] References Cited

U.S. PATENT DOCUMENTS

| | | | |
|---|---|---|---|
| 2,882,273 | 4/1959 | Holdrege et al. | 260/294 |
| 5,696,121 | 12/1997 | Bishop | 514/254 |
| 5,719,148 | 2/1998 | Bishop | 514/228.2 |

FOREIGN PATENT DOCUMENTS

| | | |
|---|---|---|
| 0 396 083 | 11/1990 | European Pat. Off. |
| 76596 | 7/1894 | Germany. |
| 367611 | 4/1923 | Germany. |
| 95 10515 | 7/1995 | WIPO. |
| 95 10516 | 7/1995 | WIPO. |
| 96 30018 | 10/1996 | WIPO. |
| 96 30363 | 10/1996 | WIPO. |
| 96 31478 | 10/1996 | WIPO. |
| WO 97/23478 | 7/1997 | WIPO. |

OTHER PUBLICATIONS

Rabjohn N. et al. Organic synthesis. Collective vol. 4. John Wiley & Sons, Inc. New York. pp. 52–54, 1963.
Troyanskii El et al. Izv. Akad. Nauk SSSR, Ser. Khim. 11, pp. 2537–2546, 1985.
The Merck Index. 9$^{th}$ Edition. p. 1266, 1976.
Buchel, et al., Methoden der Organischen Chemie, Georg Thieme Verlag Stuttgart, pp. 343–344, (1983).
Davis et al., J. Am. Chem. Soc., 45, 1816 (1923).
Bachmann et al., J. Am. Chem. Soc., 72, 3132 (1950).
Yu et al., Chem. Heterocycl. Compd., 27 (9), 999 (1991).
Troyanskii et al., Bull. Acad. Sci. USSR, Div. Chem. Sci., (English Translation), V. 34 (8), 1656–1661 (1985).
Baumann et al., Chem. Ber., I, pp. 34–38 (1874).
Baumann J. Bio. Chem., 21, pp. 563–566 (1915).
Moersch et al., J.A.C.S., vol. 69, pp. 2619–2621 (1947).
Weisel et al., J.A.C.S., vol. 67, pp. 1055–1056 (1945).

*Primary Examiner*—Evelyn Huang
*Attorney, Agent, or Firm*—Henry C. Jeanette

[57] ABSTRACT

The invention relates to a process for producing a carboxamide of the formula

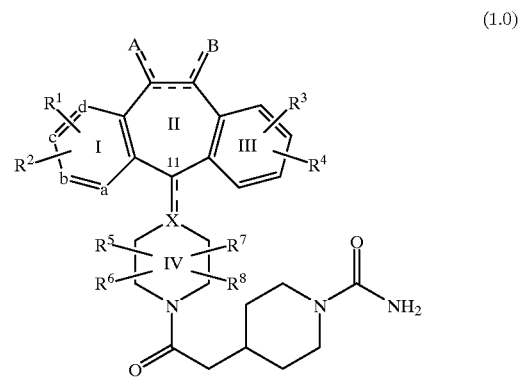

(1.0)

which comprises reacting

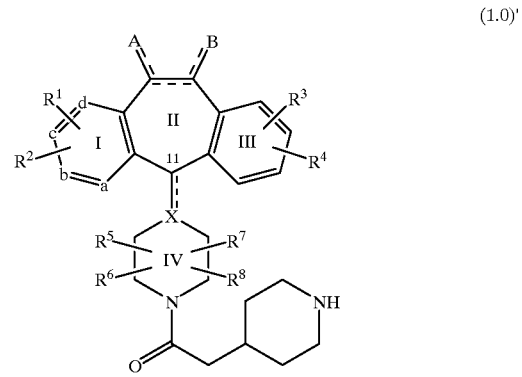

(1.0)' with an excess of urea in water, wherein the variables in the above formulae are as described herein.

16 Claims, No Drawings

METHOD FOR PREPARING CARBOXAMIDES

REFERENCE TO RELATED APPLICATIONS

This application claims the benefit of U.S. Provisional Application Ser. No. 60/021,009 filed Jul. 26, 1996, and U.S. Provisional Application Ser. No. 60/028,926 filed Sep. 13, 1996.

SUMMARY OF THE INVENTION

This invention provides an improved process for producing the compounds of the formula (1.0):

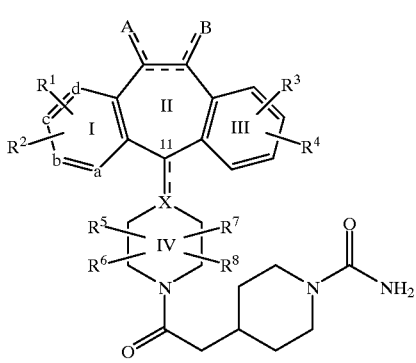

(1.0)

wherein all substituents are as described below,
which comprises reacting a compound of the formula (1.0)'

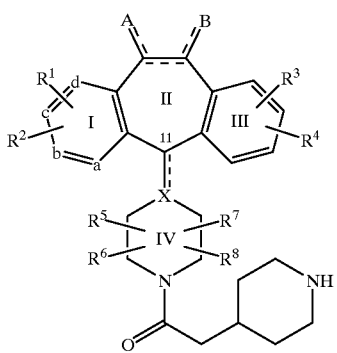

(1.0)' with an excess of urea in water.

The compounds of formula (1.0) are useful for inhibiting tumor growth. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

The compounds of formula (1.0) are disclosed in copending application Ser. No. 08/410,187 filed Mar. 24, 1995, which is hereby incorporated by reference.

The compounds of formula (1.0)' may be prepared by procedures disclosed in WO 95/10516 published Apr. 20, 1995, which is hereby incorporated by reference.

Compounds of the invention may be prepared according to the procedures described in WO 95/10516 published Apr. 20, 1995, copending Application Ser. No. 08/410,187 filed Mar. 24, 1995, copending Application Ser. No. 08/577,951 filed Dec. 22, 1995, and copending Application Ser. No. 08/615,760 filed Mar. 13, 1996; the disclosures of each being incorporated herein by reference thereto; and according to the procedures described below.

The preparation of certain starting materials of the formula (1.0)' is described in the preparatory examples below. All starting materials of the formula (1.0)' can be prepared by the methods described in the preparatory examples below, or by methods analogous to those described in the preparatory examples below. Moreover, the preparation of final products of the formula (1.0) are also described in the preparatory examples below.

DETAILED DESCRIPTION OF THE INVENTION

This invention provides an improved process for producing the compounds of the formula (1.0):

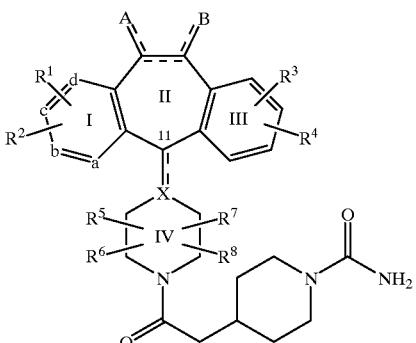

(1.0)

which comprises reacting a compound of formula(1.0)'

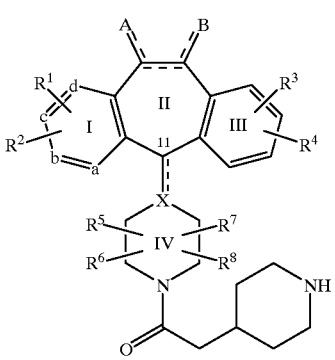

(1.0)' with an excess of urea in water;
wherein:
X is N, CH, or C when the double bond is present at the C-11 position;
one of a, b, c and d represents N or $NR^9$ wherein $R^9$ is $O^-$, $—CH_3$ or $—(CH_2)_nCO_2H$ wherein n is 1 to 3, and the remaining a, b, c and d groups represent $CR^1$ or $CR^2$; or
each of a, b, c, and d are independently selected from $CR^1$ or $CR^2$;
each $R^1$ and each $R^2$ is independently selected from H, halo, $—CF_3$, $—OR^{10}$ (e.g., $—OCH_3$), $—COR^{10}$, $—SR^{10}$ (e.g., $—SCH_3$ and $—SCH_2C_6H_5$), $—S(O)_tR^{11}$ (wherein t is 0, 1 or 2, e.g., —SOCH$_3$ and —SO$_2$CH$_3$), —SCN, —N(R$^{10}$)$_2$, —NR$^{10}$R$^{11}$, —NO$_2$, —OC(O)R$^{10}$, —CO$_2$R$^{10}$, —OCO$_2$R$^{11}$, —CN, —NHC(O)R$^{10}$, —NHSO$_2$R$^{10}$, —CONHR$^{10}$, —CONHCH$_2$CH$_2$OH, —NR$^{10}$COOR$^{11}$,

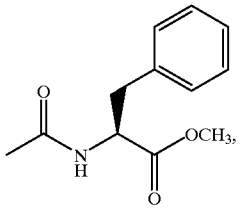

—SR$^{11}$C(O)OR$^{11}$ (e.g., —SCH$_2$CO$_2$CH$_3$), —SR$^{11}$ N(R$^{12}$)$_2$ wherein each R$^{12}$ is independently selected from H and —C(O)OR$^{11}$ (e.g., —S(CH$_2$)$_2$NHC(O)O-t-butyl and —S(CH$_2$)$_2$NH$_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, —OR$^{10}$ or —CO$_2$R$^{10}$;

R$^3$ and R$^4$ are the same or different and each independently represents H, any of the substituents of R$^1$ and R$^2$, or R$^3$ and R$^4$ taken together represent a saturated or unsaturated C$_5$–C$_7$ fused ring to the benzene ring (Ring III);

R$^5$, R$^6$, R$^7$ and R$^8$ each independently represents H, —CF$_3$, —COR$^{10}$, alkyl or aryl, said alkyl or aryl optionally being substituted with —OR$^{10}$, —SR$^{10}$, —S(O)$_t$R$^{11}$, —NR$^{10}$COOR$^{11}$, —N(R$^{10}$)$_2$, —NO$_2$, —COR$^{10}$, —OCOR$^{10}$—OCO$_2$R$^{11}$, —CO$_2$R$^{10}$, OPO$_3$R$^{10}$, or R$^5$ is combined with R$^6$ to represent =O or =S and/or R$^7$ is combined with R$^8$ to represent =O or =S;

R$^{10}$ represents H, alkyl, aryl, or aralkyl (e.g., benzyl);

R$^{11}$ represents alkyl or aryl;

the dotted line between carbon atoms 5 and 6 represents an optional double bond, such that when a double bond is present, A and B independently represent —R$^{10}$, halo, —OR$^{11}$, —OCO$_2$R$^{11}$ or —OC(O)R$^{10}$, and when no double bond is present between carbon atoms 5 and 6, A and B each independently represent H$_2$, —(OR$^{11}$)$_2$; H and halo, dihalo, alkyl and H, (alkyl)$_2$, —H and —OC(O)R$^{10}$, H and —OR$^{10}$, =O, aryl and H, =NOR$^{10}$ or —O—(CH$_2$)$_p$—O— wherein p is 2, 3 or 4.

This process comprises reacting compounds of formula (1.0)' as described above with excess urea in water to obtain the compounds of formula (1.0)

A preferred process of the invention comprises using a compound of formula (1.0') wherein a is N; R$_5$, R$_6$, R$_7$, and R$_8$ are all H; and R$_1$, R$_2$, R$_3$, and R$_4$, are each independently selected from the group consisting of H or halo.

A more preferred process of the invention comprises using a compound of formula (1.0') as described just above wherein R$_1$, is H; and R$_2$ is Br; and R$_3$, and R$_4$, are each independently selected from the group consisting of Br and Cl.

A more preferred process of the invention comprises using a compound of formula (1.0') as described just above wherein X is CH.

A more preferred process of the invention comprises using a compound of formula (1.0') as described just above wherein R$_3$ is Br; and R$_4$, is Cl.

In a more specific embodiment, this invention provides a process for producing compounds of the formulae:

I

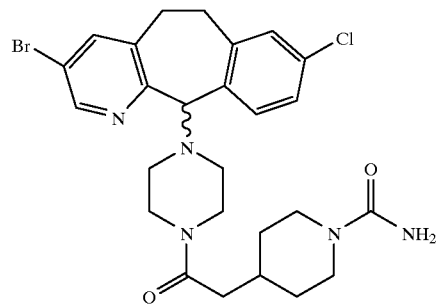

and

III

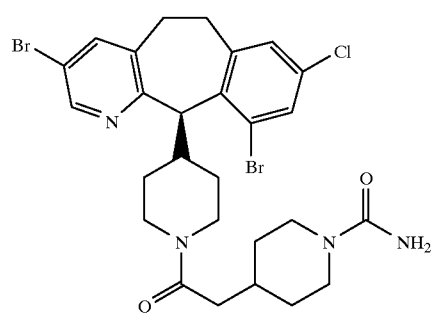

which comprises reacting either II or IV

II

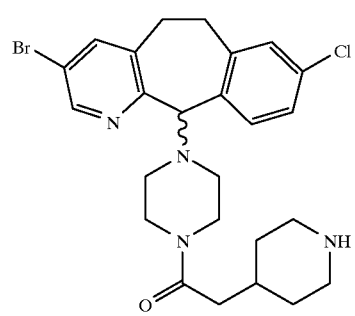

or

IV

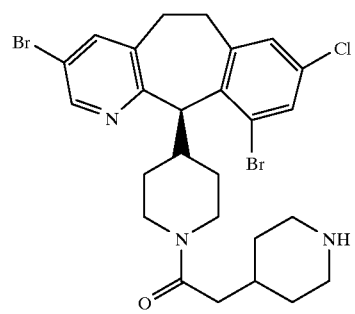

with an excess of urea in water. This reaction is run with about 4 to about 10 equivalents of urea as compared to the compounds of formula II, or IV more preferably about 10 equivalents of urea. The reaction is run for about 3 to about 68 hours, more preferably about 60 to 70 hours. The reaction is usually run at the reflux temperature of the reaction mixture. This can range from about 98 to about 100° C. The ratio of reactants II or IV to water may typically vary from about 0.025 g/ml to about 0.6 g/ml more preferably about 0.1 g/ml. The respective carboxamides of formulae I and III so obtained can be isolated by conventional means such as evaporation of the reaction mixture followed by chromatography on silica gel.

The process of the invention is typically run with the reactants II or IV which are insoluble in water, in a heterogeneous mixture with the aqueous urea solution. Typically, the reactants II or IV may partially, or fully melt at some point during the reaction, but the reaction remains heterogeneous.

All of the compounds of formula (1.0) above can be prepared using the procedures described above, or can be prepared by procedures analogous to those described just above.

Literature procedures (F. Kurzer, Org. Synth., Collec., Vol. 4, 52 (1953)) require the conversion of water insoluble amines into their acid addition salts, which is usually done in situ in order to obtain water soluble forms of the amine for reaction with aqueous solutions of urea at about 100° C. The present process of the invention is carried out without the formation of the acid addition salts of the amine.

As used herein, alkyl-(including the alkyl portions of alkoxy, alkylamino and dialkylamino)-represents straight and branched carbon chains and contains from one to twenty carbon atoms, preferably one to six carbon atoms;

alkanediyl-represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —$CH_2CH_2CH_2$—, —$CH_2CHCH_3$, —$CHCH_2CH_3$, etc.

cycloalkyl-represents saturated carbocyclic rings branched or unbranched of from 3 to 20 carbon atoms, preferably 3 to 7 carbon atoms;

alkenyl-represents straight and branched carbon chains having at least one carbon to carbon double bond and containing from 2 to 12 carbon atoms, preferably from 2 to 6 carbon atoms and most preferably from 3 to 6 carbon atoms;

alkynyl-represents straight and branched carbon chains having at least one carbon to carbon triple bond and containing from 2 to 12 carbon atoms, preferably from 2 to 6 carbon atoms;

aryl (including the aryl portion of aryloxy and aralkyl)-represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —$COOR^{10}$ or —$NO_2$; and halo-represents fluoro, chloro, bromo and iodo; and Reference to the position of the substituents $R^1$, $R^2$, $R^3$, and $R^4$ is based on the numbered ring structure:

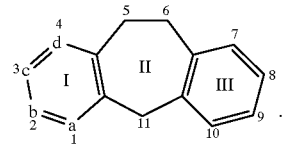

For example, $R^1$ can be at the C-4 position and $R^2$ can be at the C-2 or C-3 position. Also, for example, $R^3$ can be at the C-8 position and $R^4$ can be at the C-9 position.

When the bond from the IV ring to the C-11 carbon is a single bond, all stereoisomers are included within formula (1.0), that is, racemates, R-isomers, and S-isomers.

Compounds of Formula 1.0 include compounds wherein the bottom piperidinyl group is a 4- or 3-piperidinyl group, i.e.,

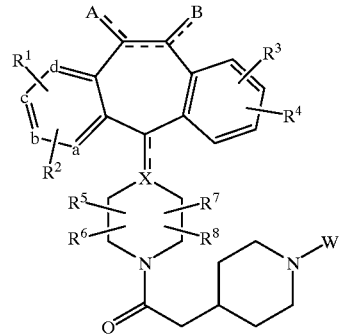

(1.1)

or

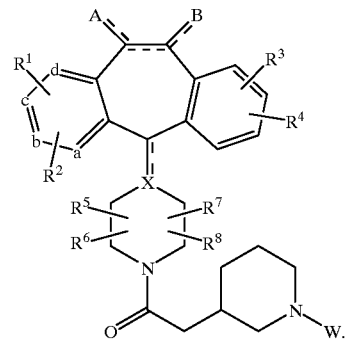

(1.1A)

Compounds of Formula 1.0 include compounds wherein $R^2$ and $R^4$ are H, and $R^1$ and $R^3$ are halo (preferably independently selected from Br or Cl). For example, $R^1$ is Br and $R^3$ is Cl. These compounds include compounds wherein $R^1$ is in the 3-position and $R^3$ is in the 8-position, e.g., 3-Br and 8-Cl. Compounds of Formula 1.0 also include compounds wherein $R^2$ is H, and $R^1$, $R^3$ and $R^4$ are halo (preferably independently selected from Br or Cl).

Preferably, compounds of Formula 1.0 are represented by compounds of Formula 1.1:

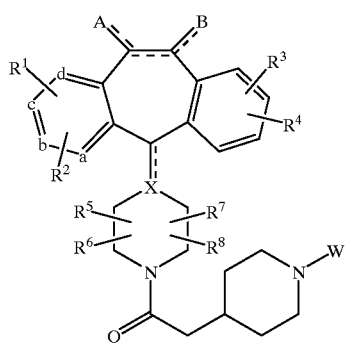

(1.1)

wherein all substituents are as defined for Formula 1.0.

Preferably, $R^2$ is H and $R^1$, $R^3$ and $R^4$ are halo; a is N and b, c and d are carbon; A and B are each $H_2$; the optional bond between C5 and C6 is absent; X is CH; and $R^5$, $R^6$, $R^7$ and $R^8$ are H. More preferably, $R^1$, $R^3$ and $R^4$ are independently selected from Br or Cl. Most preferably, $R^1$ is Br, and $R^3$ and $R^4$ are independently selected from Cl and Br.

More preferably, compounds of Formula 1.0 are represented by compounds of Formula 1.2 and Formula 1.3:

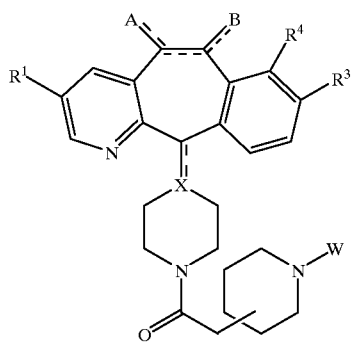

(1.2)

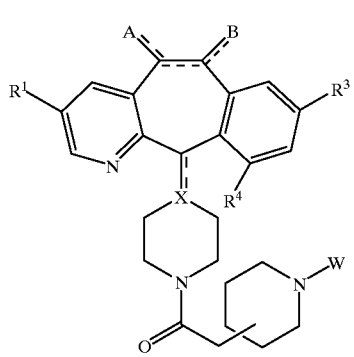

(1.3)

and most preferably, compounds of Formulas 1.4 and 1.5

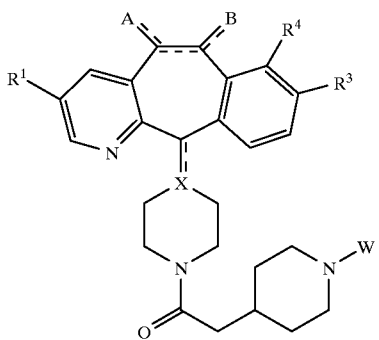

(1.4)

(1.5)

wherein $R^1$, $R^3$ and $R^4$ are each independently selected from halo, preferably, Br or Cl; and A, B, X and W are as defined for Formula 1.0. More preferably, A and B are each $H_2$; the optional bond between C5 and C6 is absent; and X is CH. Most preferably, $R^1$ is Br; $R^3$ and $R^4$ are independently Br or Cl, and still more preferably $R^3$ is Cl and $R^4$ is Br; A and B are each $H_2$; the optional bond between C5 and C6 is absent; X is CH; and $R^5$, $R^6$, $R^7$ and $R^8$ are H.

Examples of $-C(O)R^{12}$ substituents for W include groups wherein $R^{12}$ is selected from the group consisting of:

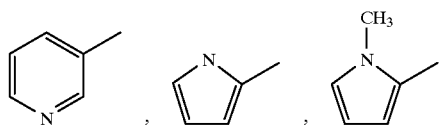

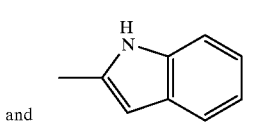

and

Examples of imidates for substituent W include groups wherein $R^{13}$ is selected from the group consisting of: (1) CN; (2) H; (3) $-SO_2NR^{15}R^{16}$ wherein $R^{15}$ and $R^{16}$ are selected from the group consisting of: H and alkyl (e.g., methyl); (4) $-C(O)NR^{15}R^{16}$ wherein $R^{15}$ and $R^{16}$ are selected from the group consisting of: H and alkyl (e.g., methyl); (5) $-SO_2$-alkyl; and (6) $-C(O)$-aryl. Examples of imidates also include groups wherein $R^{14}$ is aryl (e.g., phenyl).

For example, imidates for substituent W include groups wherein $R^{13}$ is selected from the group consisting of: CN, —C(O)NH$_2$, H, —SO$_2$NH$_2$, —SO$_2$NHCH$_3$, —SO$_2$N(CH$_3$)$_2$, —C(O)NHCH$_3$, —SO$_2$CH$_3$ and —C(O)C$_6$H$_5$. Examples of imidates also include groups wherein $R^{14}$ is phenyl; and $R^{13}$ is selected from the group consisting of: CN, —C(O)NH$_2$, H, —SO$_2$NH$_2$, —SO$_2$NHCH$_3$, —SO$_2$N(CH$_3$)$_2$, —C(O)NHCH$_3$, —SO$_2$CH$_3$ and —C(O)C$_6$H$_5$.

Examples of guanidines for substituent W include groups wherein $R^{17}$ is selected from the group consisting of: (1) CN; (2) H; (3) —OR$^{22}$; (4) —NR$^{20}$R$^{21}$ wherein $R^{20}$ and $R^{21}$ are independently selected from the group consisting of: H and alkyl (e.g., methyl); (5) —SO$_2$NR$^{20}$OR$^{21}$ wherein $R^{20}$ and $R^{21}$ are independently selected from the group consisting of: H and alkyl (e.g., methyl), (6) —C(O)NR$^{20}$R$^{21}$ wherein $R^{20}$ and $R^{21}$ are independently selected from the group consisting of: H and alkyl (e.g., methyl); (7) —SO$_2$-alkyl; and (8) —C(O)-aryl. Examples of the guanidines also include groups wherein $R^{18}$ and $R^{19}$ are selected from the group consisting of: H and heteroaralkyl.

For example, guanidines for substituent W include groups wherein $R^{17}$ is selected from the group consisting of: CN, H, —OCH$_3$, —OH, —NH$_2$, —N(CH$_3$)$_2$, —SO$_2$NH$_2$, —SO$_2$NHCH$_3$, —SO$_2$N(CH$_3$)$_2$, —C(O)NH$_2$, —C(O)NHCH$_3$, —SO$_2$CH$_3$ and —C(O)C$_6$H$_5$. Examples of guanidines also include groups wherein $R^{18}$ and $R^{19}$ are selected from the group consisting of: H and

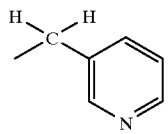

(i.e., —CH$_2$-pyrid-3-yl).

Examples of the guanidine substituents additionally include groups wherein: $R^{18}$ and $R^{19}$ are selected from the group consisting of: H and —CH$_2$-pyrid-3-yl; and $R^{17}$ is selected from the group consisting of: CN, H, —OCH$_3$, —OH, —NH$_2$, —N(CH$_3$)$_2$, —SO$_2$NH$_2$, —SO$_2$NHCH$_3$, —SO$_2$N(CH$_3$)$_2$, —C(O)NH$_2$, —C(O)NHCH$_3$, —SO$_2$CH$_3$ and —C(O)C$_6$H$_5$.

In addition, examples of the guanidine substituents additionally include groups wherein: (1) $R^{17}$ and $R^{18}$ are H, and $R^{19}$ is —CH$_2$-pyrid-3-yl; and (2) $R^{18}$ and $R^{19}$ are H, and $R^{17}$ is selected from the group consisting of: CN, H, —OCH$_3$, —OH, —NH$_2$, —N(CH$_3$)$_2$, —SO$_2$NH$_2$, —SO$_2$NHCH$_3$, —SO$_2$N(CH$_3$)$_2$, —C(O)NH$_2$, —C(O)NHCH$_3$, —SO$_2$CH$_3$ and —C(O)C$_6$H$_5$.

Examples of 1-amino-2-nitroethylene derivatives for substituent W include groups wherein $R^{26}$ is alkyl, e.g., methyl.

Those skilled in the art will appreciate that compounds of Formula 1.0 include compounds of Formulas 1.0A and 1.0B:

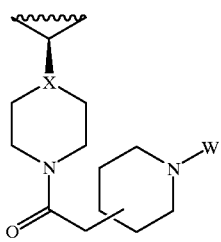

(1.0A)

and

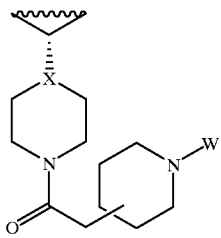

(1.0B)

wherein X is CH or N, with compounds of 1.0A being preferred when X is CH, and with compounds of 1.0B being preferred when X is N.

The preferred compounds of this invention are represented by the compounds of Formulas:

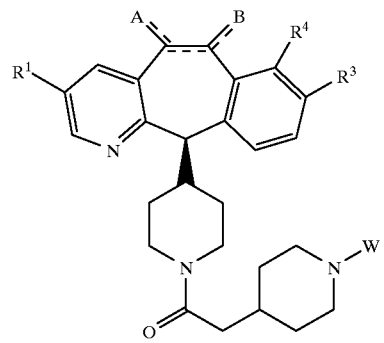

(1.4A)

and

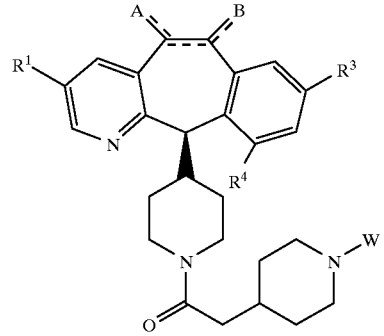

(1.5A)

wherein the substituents are as defined above, with the compounds of Formula 1.5A being more preferred.

The examples illustrate the process of this invention:

PREPARATORY EXAMPLES

PREPARATIVE EXAMPLE 1

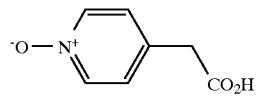

Step A:

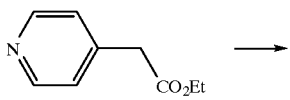 →

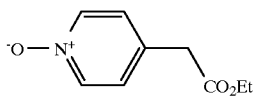

Combine 10 g (60.5 mmol) of ethyl 4-pyridylacetate and 120 mL of dry $CH_2Cl_2$ at −20° C., add 10.45 g (60.5 mmol) of MCPBA and stir at −20° C. for 1 hour and then at 25° C. for 67 hours. Add an additional 3.48 g (20.2 mmoles) of MCPBA and stir at 25° C. for 24 hours. Dilute with $CH_2Cl_2$ and wash with saturated $NaHCO_3$ (aqueous) and then water. Dry over $MgSO_4$, concentrate in vacuo to a residue, and chromatograph (silica gel, 2%–5.5% (10% $NH_4OH$ in MeOH)/$CH_2Cl_2$) to give 8.12 g of the product compound. Mass Spec.: $MH^+$=182.15

Step B:

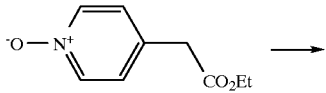 →

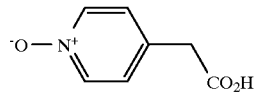

Combine 3.5 g (19.3 mmol) of the product of Step A, 17.5 mL of EtOH and 96.6 mL of 10% NaOH (aqueous) and heat the mixture at 67° C. for 2 hours. Add 2N HCl (aqueous) to adjust to pH=2.37 and concentrate in vacuo to a residue. Add 200 mL of dry EtOH, filter through celite® and wash the filter cake with dry EtOH 2×50 ml). Concentrate the combined filtrates in vacuo to give 2.43 g of the title compound.

PREPARATIVE EXAMPLE 2

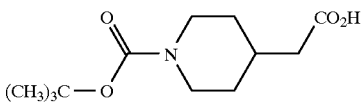

The title compound is prepared via the process disclosed in PCT International Publication No. WO95/10516.

PREPARATIVE EXAMPLE 3

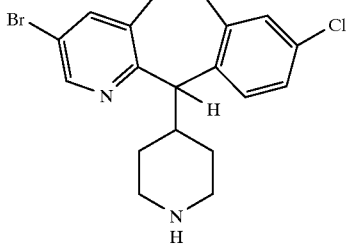

Step A:

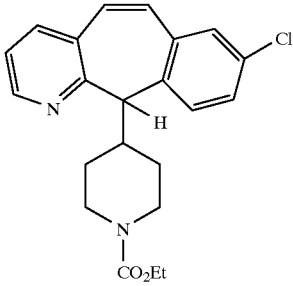 →

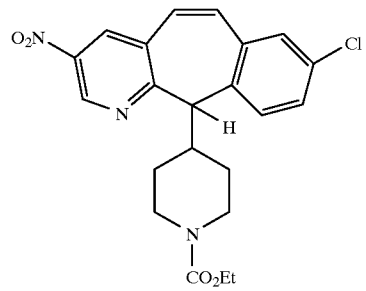

3A(i)

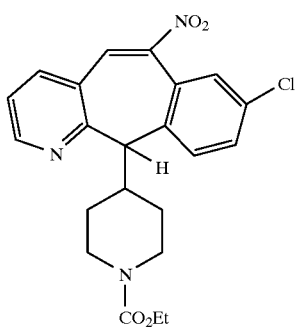

3A(ii)

Combine 14.95 g (39 mmol) of 8-chloro-11-(1-ethoxy-carbonyl-4-piperidinyl)-11H-benzo[5,6]cyclohepta[1,2-b]pyridine and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 3A(i) and 3A(ii), respectively.

Mass Spec. for compound 3A(i): MH⁺=428.2;

Mass Spec. for compound 3A(ii): MH⁺=428.3

Step B:

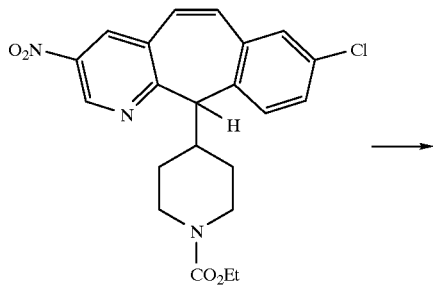

Combine 22.0 g (51.4 mmol) of the product 3A(i) from Step A, 150 mL of 85% EtOH (aqueous), 25.85 g (0.463 mole) of Fe powder and 2.42 g (21.8 mmol) of CaCl$_2$, and heat at reflux overnight. Add 12.4 g (0.222 mole) of Fe powder and 1.2 g (10.8 mmol) of CaCl$_2$ and heat at reflux for 2 hours. Add another 12.4 g (0.222 mole) of Fe powder and 1.2 g (10.8 mmol) of CaCl$_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, MeOH/CH$_2$Cl$_2$ gradient) to give 16.47 g of the product compound.

Step C:

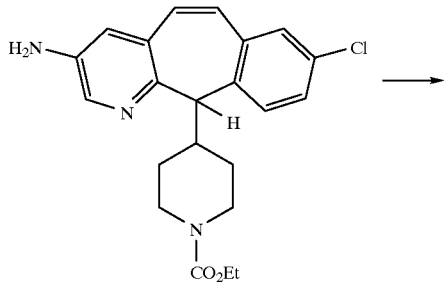

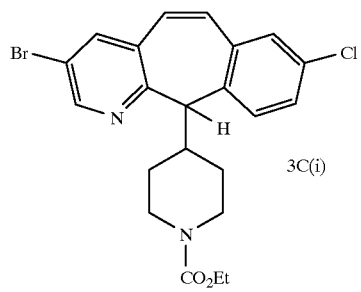

3C(i)

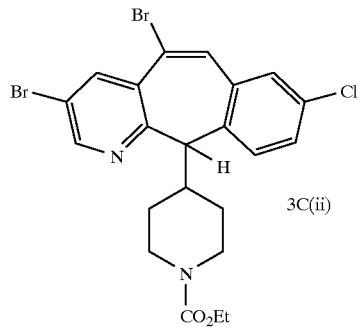

3C(ii)

Combine 16.47 g (41.4 mmol) of the product from Step B, and 150 mL of 48% HBr (aqueous) and cool to −3° C. Slowly add (dropwise) 18 mL of bromine, then slowly add (dropwise) a solution of 8.55 g (0.124 mole) of NaNO$_3$ in 85 mL of water. Stir for 45 minutes at −3° to 0° C., then adjust to pH=10 by adding 50% NaOH (aqueous). Extract with EtOAc, wash the extracts with brine and dry the extracts over Na$_2$SO$_4$. Concentrate to a residue and chromatograph (silica gel, EtOAc/hexane gradient) to give 10.6 g and 3.28 g of the two product compounds 3C(i) and 3C(ii), respectively.

Mass Spec. for compound 3C(i): MH⁺=461.2;

Mass Spec. for compound 3C(ii): MH⁺=539

Step D:

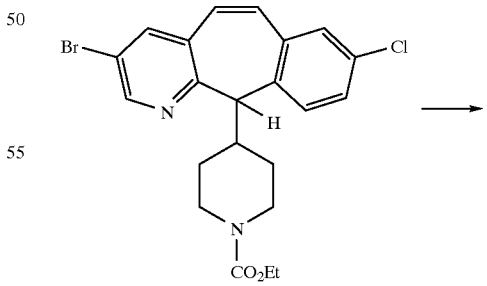

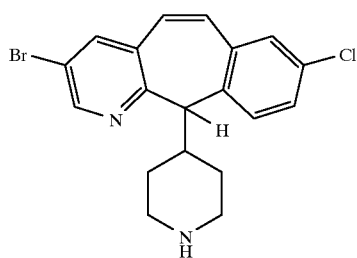

Hydrolyze the product 3C(i) of Step C by dissolving in concentrated HCl and heating to about 100° C. for @ 16 hours. Cool the mixture, the neutralize with 1M NaOH (aqueous). Extract with CH₂Cl₂, dry the extracts over MgSO₄, filter and concentrate in vacuo to the title compound.

Mass Spec.: MH⁺=466.9

PREPARATIVE EXAMPLE 4

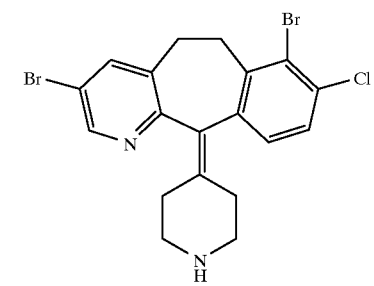

Step A:

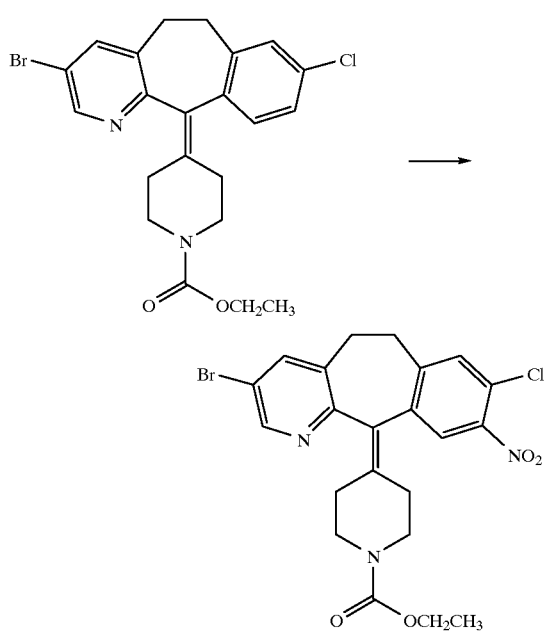

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated H₂SO₄ at −5° C., then add 4.8 g (56.4 mmol) of NaNO₃ and stir for 2 hours. Pour the mixture into 600 g of ice and basify with concentrated NH₄OH (aqueous). Filter the mixture, wash with 300 mL of water, then extract with 500 mL of CH₂Cl₂. Wash the extract with 200 mL of water, dry over MgSO₄, then filter and concentrate in vacuo to a residue. Chromatograph the residue (silica gel, 10% EtOAc/CH₂Cl₂) to give 24.4 g (86% yield) of the product. m.p.=165°–167° C., Mass Spec.: MH⁺=506, 508 (Cl).

elemental analysis: calculated-C, 52.13; H, 4.17; N, 8.29 found-C, 52.18; H, 4.51; N, 8.16

Step B:

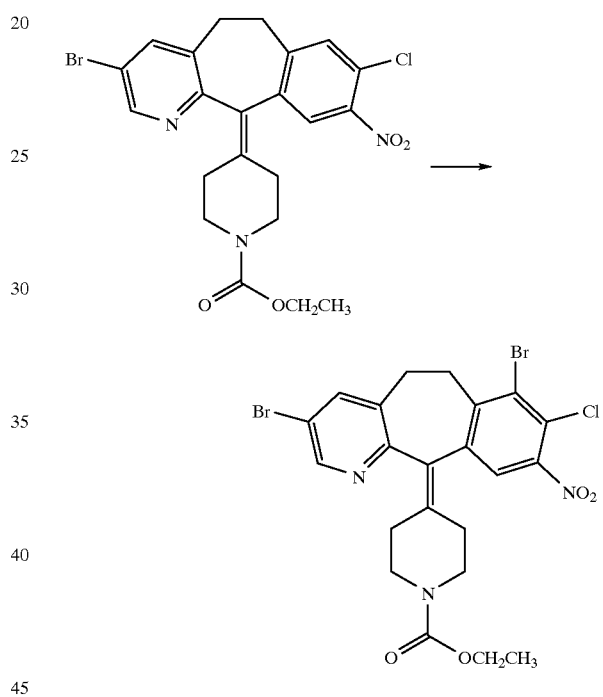

Combine 20 g (40.5 mmol) of the product of Step A and 200 mL of concentrated H₂SO₄ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated NH₄OH (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: MH⁺=586 (Cl).

elemental analysis: calculated-C, 45.11; H, 3.44; N, 7.17 found-C, 44.95; H, 3.57; N, 7.16

Step C:

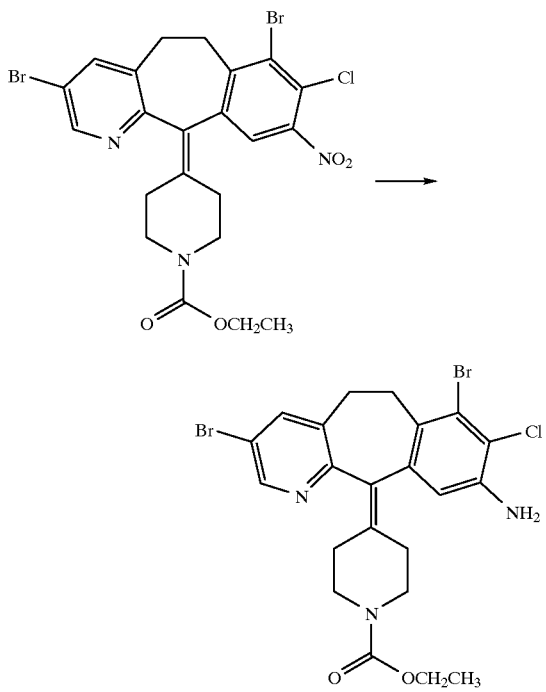

Combine 25 g (447 mmol) of Fe filings, 10 g (90 mmol) of CaCl$_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH$_2$Cl$_2$, wash with 300 mL of water and dry over MgSO$_4$. Filter and concentrate in vacuo to a residue, then chromatograph (silica gel, 30% EtOAc/CH$_2$Cl$_2$) to give 11.4 g (60% yield) of the product. m.p.=211–212° C., Mass Spec.: MH$^+$=556 (Cl).

elemental analysis: calculated-C, 47.55; H, 3.99; N, 7.56
found-C, 47.45; H, 4.31; N, 7.49

Step D:

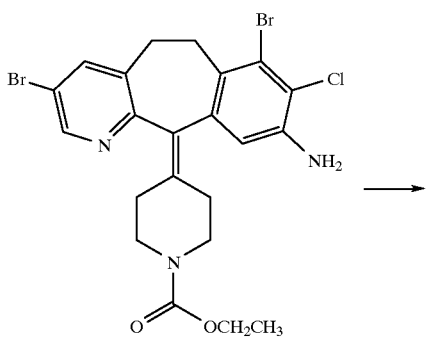

-continued

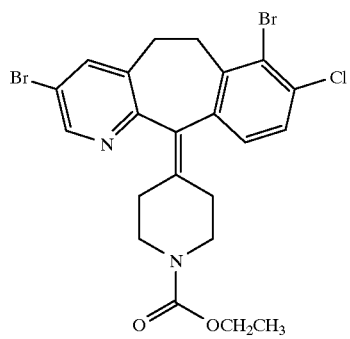

Slowly add (in portions) 20 g (35.9 mmol) of the product of Step C to a solution of 8 g (116 mmol) of NaNO$_2$ in 120 mL of concentrated HCl (aqueous) at −10° C. Stir the resulting mixture at 0° C. for 2 hours, then slowly add (dropwise) 150 mL (1.44 mole) of 50% H$_3$PO$_2$ at 0° C. over a 1 hour period. Stir at 0° C. for 3 hours, then pour into 600 g of ice and basify with concentrated NH$_4$OH (aqueous). Extract with 2×300 mL of CH$_2$Cl$_2$, dry the extracts over MgSO$_4$, then filter and concentrate in vacuo to a residue. Chromatograph the residue (silica gel, 25% EtOAc/hexanes) to give 13.67 g (70% yield) of the product. m.p.=163–165° C., Mass Spec.: MH$^+$=541 (Cl).

elemental analysis: calculated-C, 48.97; H, 4.05; N, 5.22
found-C, 48.86; H, 3.91; N, 5.18

Step E:

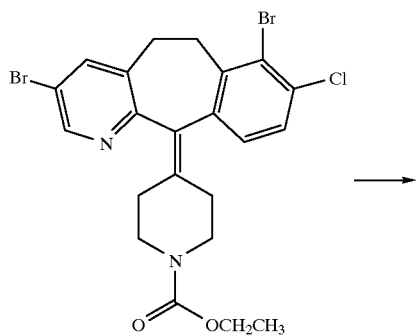

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH⁺=469 (FAB).

elemental analysis: calculated-C, 48.69; H, 3.65; N, 5.97
found-C, 48.83; H, 3.80; N, 5.97

PREPARATIVE EXAMPLE 5

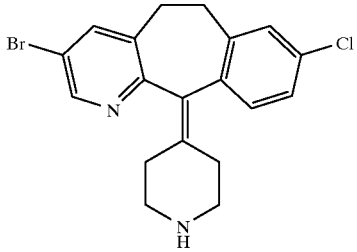

Step A:

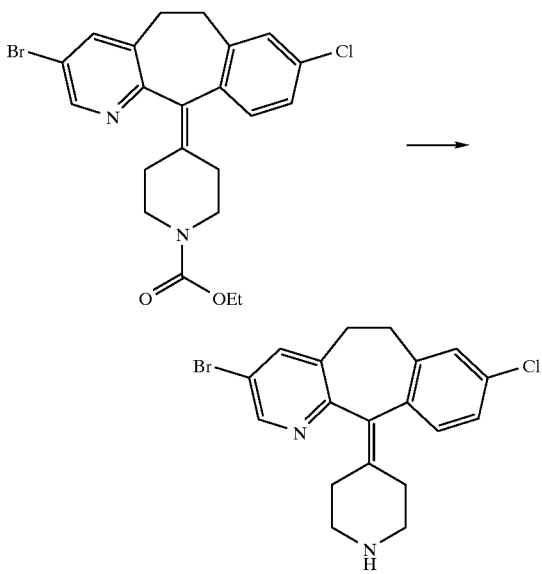

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 3, Step D, to give 1.39 g (69% yield) of the product.

Step B:

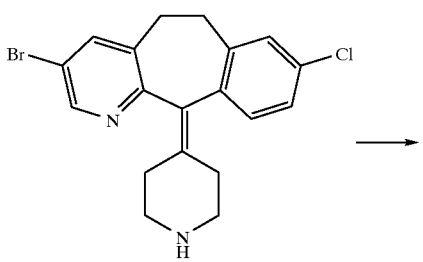

-continued

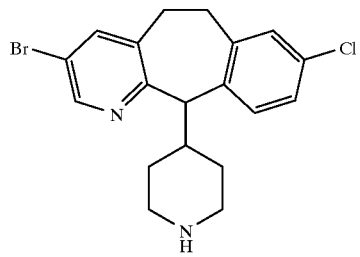

Combine 1 g (2.48 mmol) of the product of Step A and 25 mL of dry toluene, add 2.5 mL of 1M DIBAL in toluene and heat the mixture at reflux. After 0.5 hours, add another 2.5 mL of 1M DIBAL in toluene and heat at reflux for 1 hour. (The reaction is monitored by TLC using 50% MeOH/CH$_2$Cl$_2$+NH$_4$OH (aqueous).) Cool the mixture to room temperature, add 50 mL of 1N HCl (aqueous) and stir for 5 min. Add 100 mL of 1N NaOH (aqueous), then extract with EtOAc (3×150 mL). Dry the extracts over MgSO$_4$, filter and concentrate in vacuo to give 1.1 g of the title compound.

PREPARATIVE EXAMPLE 6

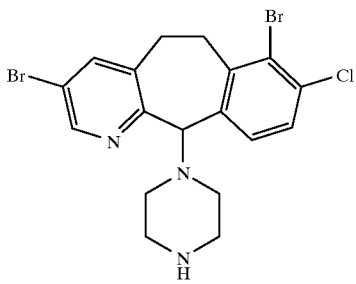

[racemic as well as (+)- and (-)- isomers]

Step A:

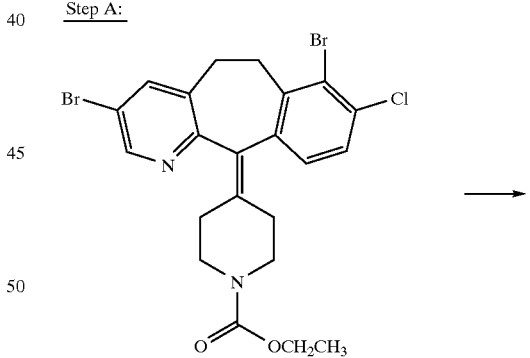

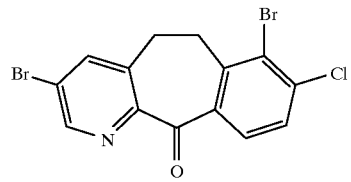

Combine 16.6 g (0.03 mole) of the product of Preparative Example 4, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield)

of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Step B:

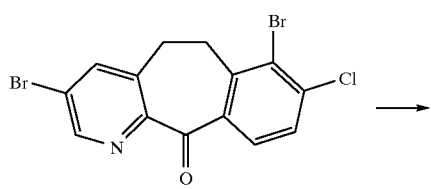

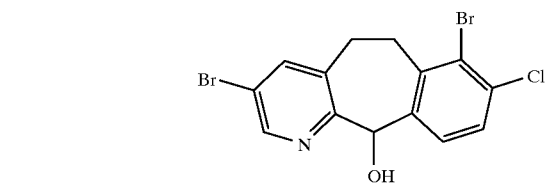

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH≈4–5 with 1M HCl (aqueous) while keeping the temperature <10° C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

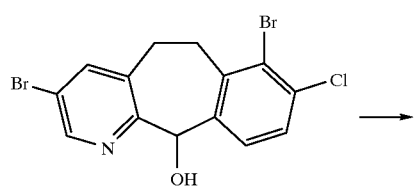

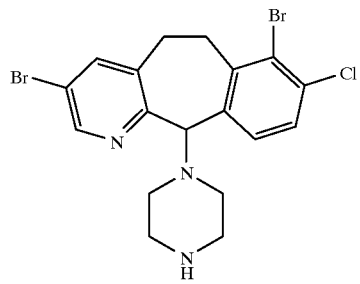

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 9 (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 g of the title compound as a racemic mixture.

Step D - Separation of Enantiomers:

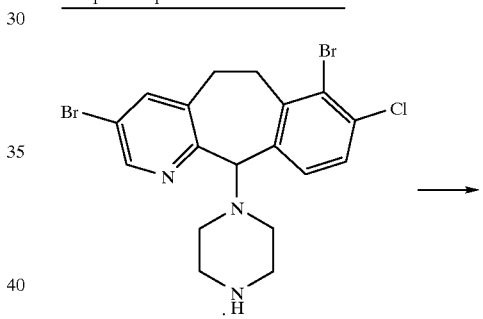

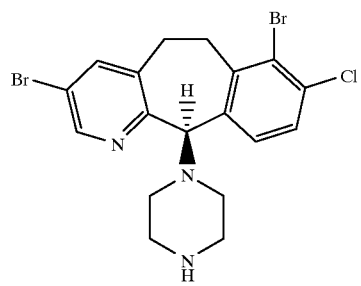

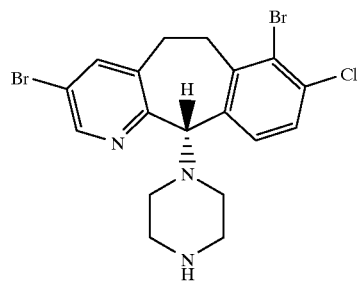

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. MH$^+$=471.9; $[a]_D^{25}$=+97.4° (8.48 mg/2mL MeOH).

Physical chemical data for (−)-isomer: m.p.=82.9°–84.5° C.; Mass Spec. MH$^+$=471.8; $[a]_D^{25}$=−97.4° (8.32 mg/2mL MeOH).

PREPARATIVE EXAMPLE 7

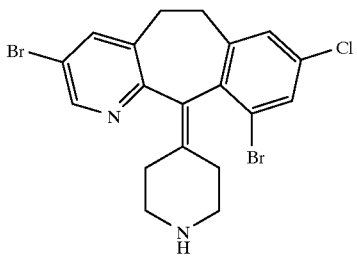

Step A:

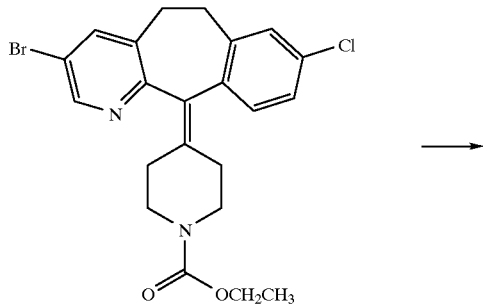

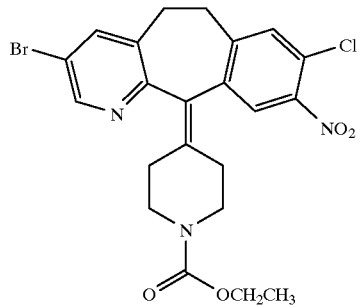

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product. $^1$H NMR (CDCl$_3$, 200 MHz): 8.5 (s, 1H); 7.7 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

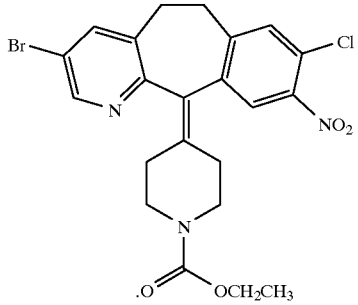

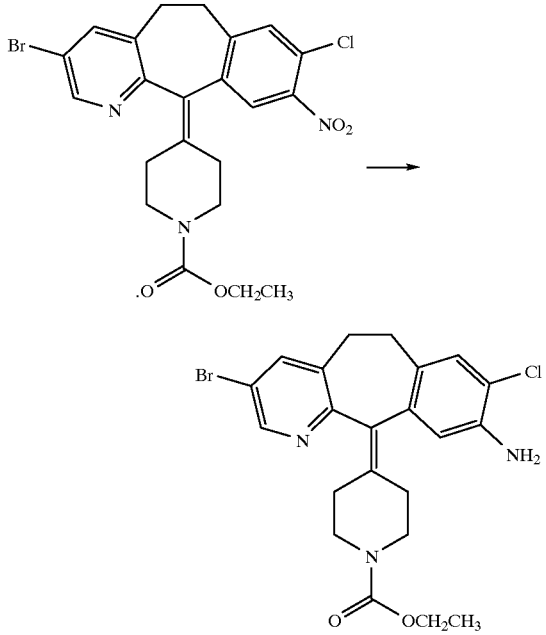

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

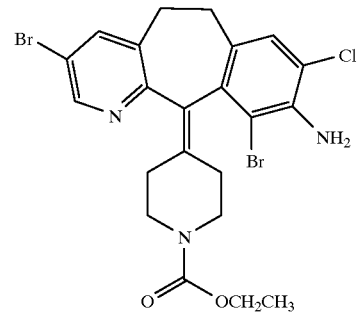

Combine 7.70 g of the product of Step B and 35 mL of HOAc, then add 45 mL of a solution of Br$_2$ in HOAc and stir the mixture at room temperature overnight. Add 300 mL of 1N NaOH (aqueous), then 75 mL of 50% NaOH (aqueous) and extract with EtOAc. Dry the extract over MgSO and concentrate in vacuo to a residue. Chromatograph the residue (silica gel, 20%–30% EtOAc/hexane) to give 3.47 g of the product (along with another 1.28 g of partially purified product). Mass Spec.: MH$^+$=555.9.

$^1$H NMR (CDCl$_3$, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D:

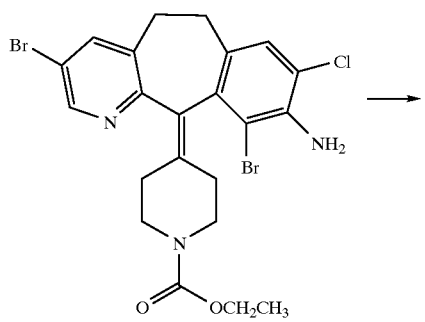

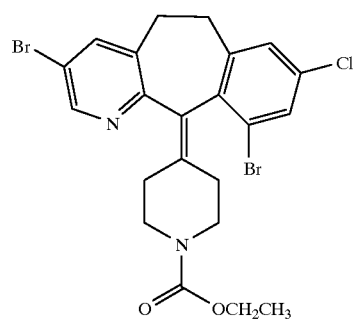

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH$_2$Cl$_2$, dry the extract over MgSO$_4$ and concentrate in vacuo to a residue. Chromatograph the residue (silica gel, 10%–20% EtOAc/hexane) to give 0.74 g of the product. Mass Spec.: MH$^+$=541.0.

$^1$H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

Step E:

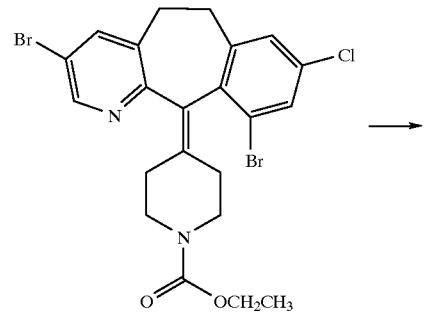

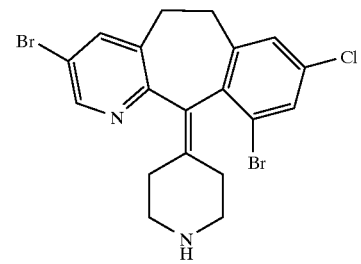

Combine 0.70 g (1.4 mmol) of the product of Step D and 8 mL of concentrated HCl (aqueous) and heat the mixture at reflux overnight. Add 30 mL of 1N NaOH (aqueous), then 5 mL of 50% NaOH (aqueous) and extract with CH$_2$Cl$_2$. Dry the extract over MgSO$_4$ and concentrate in vacuo to give 0.59 g of the title compound. Mass Spec.: M$^{+=}$468.7. m.p.= 123.9°–124.2° C.

PREPARATIVE EXAMPLE 8

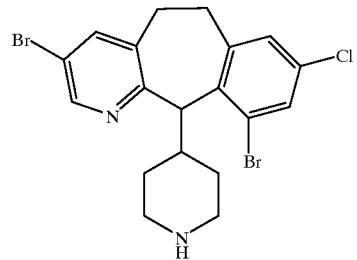

[racemic as well as (+)- and (-)-isomers]

Step A:

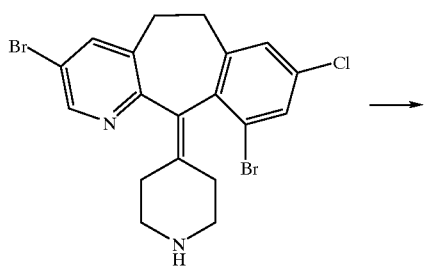

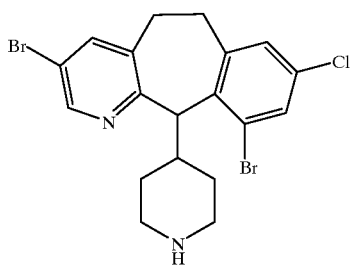

Prepare a solution of 8.1 g of the title compound from Preparative Example 7 in toluene and add 17.3 mL of a 1M solution of DIBAL in toluene. Heat the mixture at reflux and slowly add (dropwise) another 21 mL of 1M DlBAL/toluene solution over a period of 40 min. Cool the reaction mixture to about 0° C. and add 700 mL of 1M HCl (aqueous). Separate and discard the organic phase. Wash the aqueous phase with $CH_2Cl_2$, discard the extract, then basify the aqueous phase by adding 50% NaOH (aqueous). Extract with $CH_2Cl_2$, dry the extract over $MgSO_4$ and concentrate in vacuo to give 7.30 g of the title compound, which is a racemic mixture of enantiomers.

Step B - Separation of Enantiomers

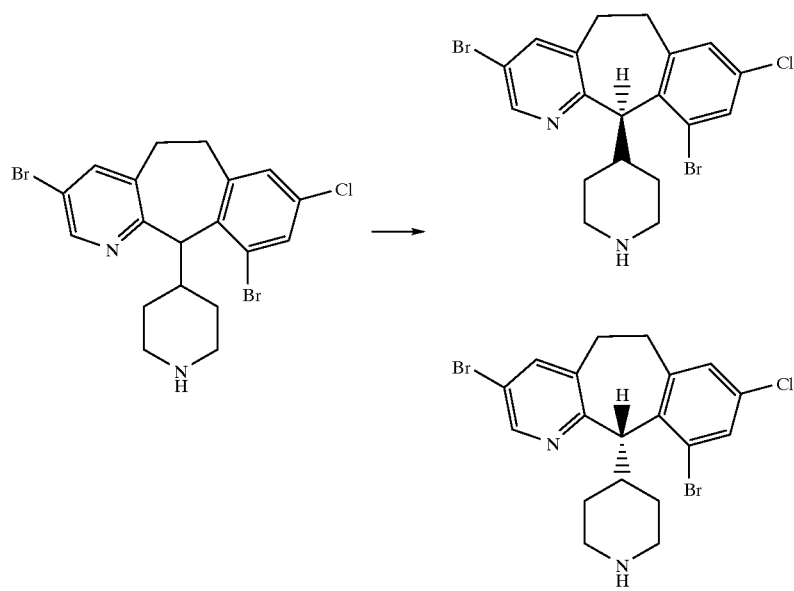

The racemic title compound of Step A is separated by preparative chiral chromatography (Chiralpack AD, 5 cm×50 cm column, using 20% iPrOH/hexane+0.2% diethylamine), to give the (+)-isomer and the (−)-isomer of the title compound.

Physical chemical data for (+)-isomer: m.p.=148.80° C.; Mass Spec. $MH^+$=472; $[a]_D^{25}$=+65.6° (mg/2mL MeOH).

Physical chemical data for (−)-isomer: m.p.=112° C.; Mass Spec. $MH^+$=472; $[a]_D^{25}$=−65.2° (mg/2mL MeOH).

PREPARATIVE EXAMPLE 9

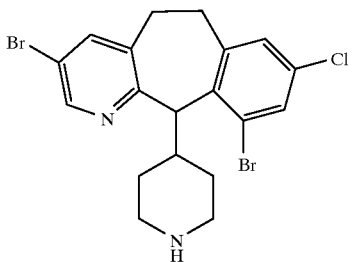

[racemic as well as (+)- and (-)-isomers]

Step A:

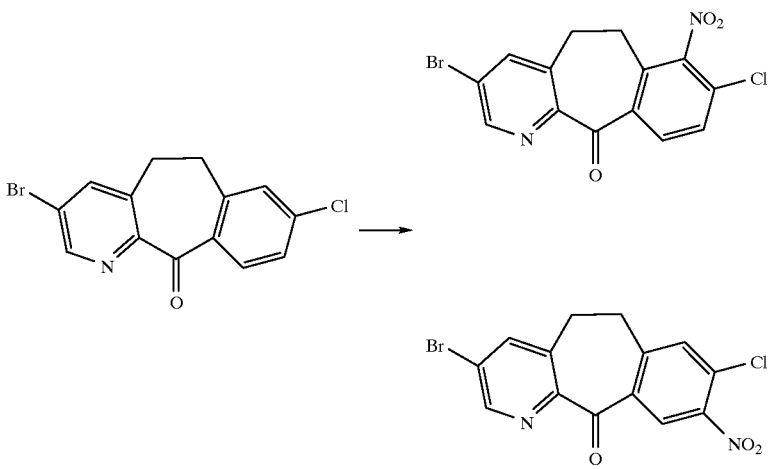

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

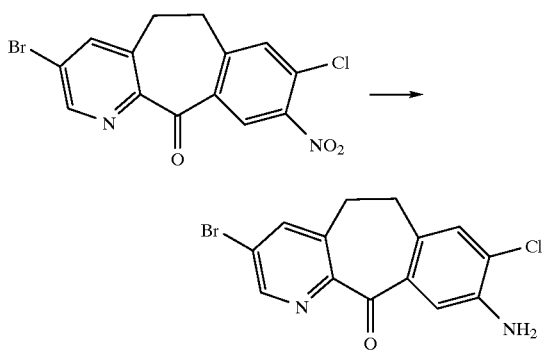

React 28 g (76.2 mmol) of the 9-nitro product of Step A, 400 mL of 85% EtOH/water, 3.8 g (34.3 mmol) of $CaCl_2$ and 38.28 g (0.685 mole) of Fe using substantially the same procedure as described for Preparative Example 4, Step C, to give 24 g of the product

Step C:

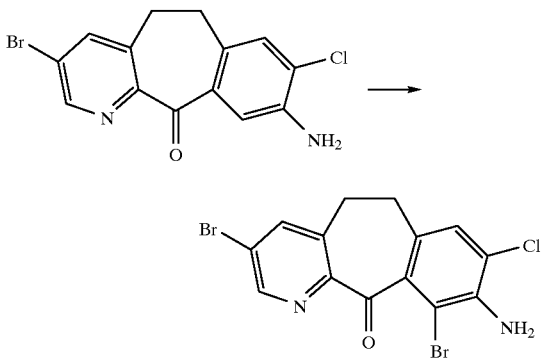

Combine 13 g (38.5 mmol) of the product of Step B, 140 mL of HOAc and slowly add a solution of 2.95 mL (57.8 mmol) of $Br_2$ in 10 mL of HOAc over a period of 20 min. Stir the reaction mixture at room temperature, then concentrate in vacuo to a residue. Add $CH_2Cl_2$ and water, then adjust to pH=8–9 with 50% NaOH (aqueous). Wash the organic phase with water, then brine and dry over $Na_2SO_4$. Concentrate in vacuo to give 11.3 g of the product.

Step D:

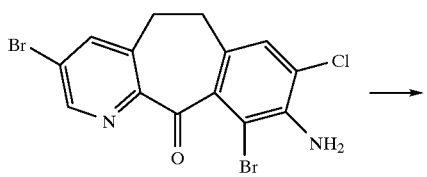

↓

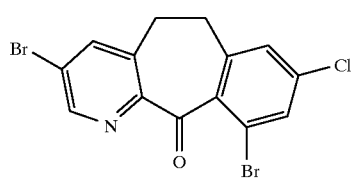

Cool 100 mL of concentrated HCl (aqueous) to 0° C., then add 5.61 g (81.4 mmol) of NaNO₂ and stir for 10 min. Slowly add (in portions) 11.3 g (27.1 mmol) of the product of Step C and stir the mixture at 0°–3° C. for 2.25 hrs. Slowly add (dropwise) 180 mL of 50% H₃PO₂ (aqueous) and allow the mixture to stand at 0° C. overnight. Slowly add (dropwise) 150 mL of 50% NaOH over 30 min., to adjust to pH=9, then extract with CH₂Cl₂. Wash the extract with water, then brine and dry over NA₂SO₄. Concentrate in vacuo to a residue and chromatograph (silica gel, 2% EtOAc/CH₂Cl₂) to give 8.6 g of the product.

Step E:

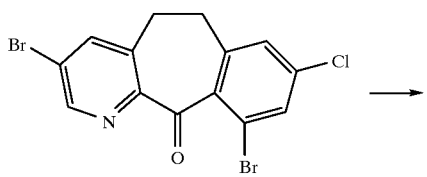

↓

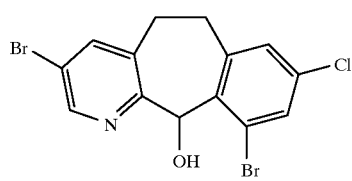

Combine 8.6 g (21.4 mmol) of the product of Step D and 300 mL of MeOH and cool to 0°–2° C. Add 1.21 g (32.1 mmol) of NaBH₄ and stir the mixture at ~0° C. for 1 hr. Add another 0.121 g (3.21 mmol) of NaBH₄, stir for 2 hr. at 0° C., then let stand overnight at 0° C. Concentrate in vacuo to a residue then partition the residue between CH₂Cl₂ and water. Separate the organic phase and concentrate in vacuo (50° C.) to give 8.2 g of the product.

Step F:

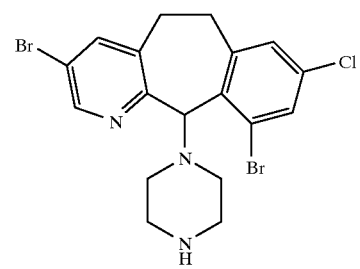

Combine 8.2 g (20.3 mmol) of the product of Step E and 160 mL of CH₂Cl₂, cool to 0° C., then slowly add (dropwise) 14.8 mL (203 mmol) of SOCl₂ over a 30 min. period. Warm the mixture to room temperature and stir for 4.5 hrs., then concentrate in vacuo to a residue, add CH₂Cl₂ and wash with 1N NaOH (aqueous) then brine and dry over Na₂SO₄. Concentrate in vacuo to a residue, then add dry THF and 8.7 g (101 mmol) of piperazine and stir at room temperature overnight. Concentrate in vacuo to a residue, add CH₂Cl₂, and wash with 0.25N NaOH (aqueous), water, then brine. Dry over Na₂SO₄ and concentrate in vacuo to give 9.46 g of the crude product. Chromatograph (silica gel, 5% MeOH/CH₂Cl₂+NH₃) to give 3.59 g of the title compound, as a racemate. ¹H NMR (CDCl₃, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G - Separation of Enantiomers:

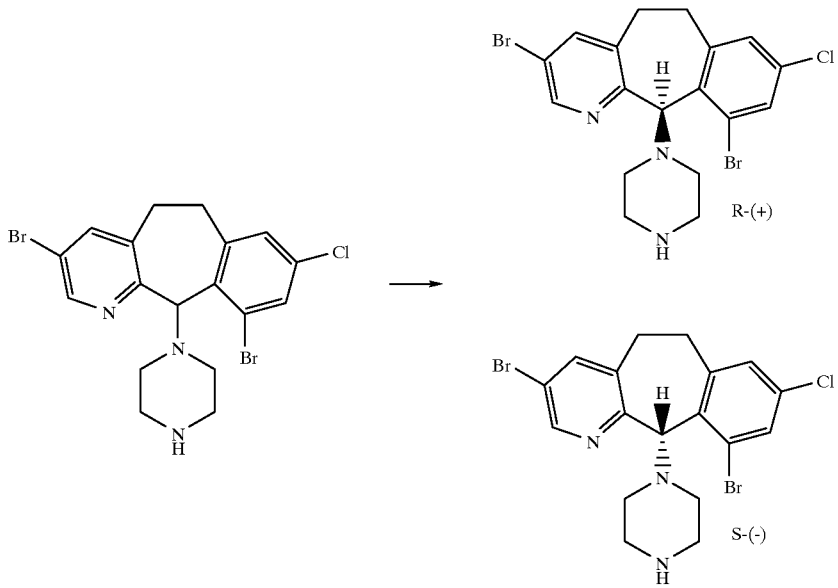

The racemic title compound from Step F (5.7 g) is chromatographed as described for Preparative Example 6, Step D, using 30% iPrOH/hexane +0.2% diethylamine, to give 2.88 g of the R-(+)-isomer and 2.77 g of the S-(−)-isomer of the title compound.

Physical chemical data for the R-(+)-isomer: Mass Spec. MH$^+$=472.0; $[a]_D^{25}$=+12.1° (10.9 mg/2mL MeOH).

Physical chemical data for the S-(−)-isomer: Mass Spec. MH$^+$=472.0; $[a]_D^{25}$=−13.2° (11.51 mg/2 mL MeOH).

PREPARATIVE EXAMPLE 10

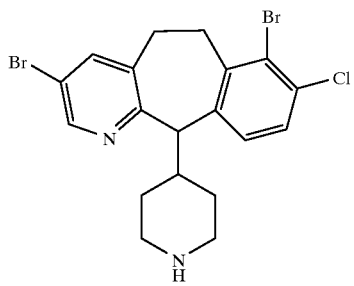

[racemic as well as (+)- and (−)-isomers]

Step A:

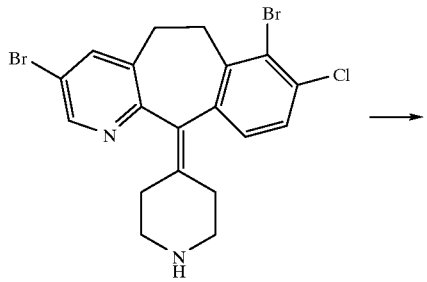

-continued

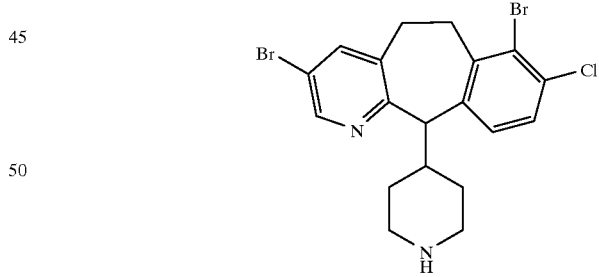

Combine 13 g (33.3 mmol) of the title compound from Preparative Example 4, Step D, and 300 mL of toluene at 20° C., then add 32.5 mL (32.5 mmol) of a 1M solution of DIBAL in toluene. Heat the mixture at reflux for 1 hr., cool to 20° C., add another 32.5 mL of 1M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with CH$_2$Cl$_2$ (3×200 mL), dry the organic layers over MgSO$_4$, then concentrate in vacuo to a residue. Chromatograph (silica gel, 12% MeOH/CH$_2$Cl$_2$+4% NH$_4$OH) to give 10.4 g of the title compound as a racemate. Mass Spec.: MH$^+$= 469/471 (FAB). partial $^1$H NMR (CDCl$_3$, 400 MHz): 8.38 (s, 1H); 7.57 (s, 1H); 7.27 (d, 1H); 7.06 (d, 1H); 3.95 (d, 1H).

Treat 4-(8-chloro-3-bromo-5,6-dihydro-11H-benzo[5,6]cyclohepta[1,2-b]pyridin-11-ylidene)- 1-piperidine-1-carboxylic acid ethyl ester via substantially the same procedure as described in Preparative Example 6, Steps A–D, to give as the product of Step C, the racemic title compound, and as the products of Step D the R-(+)-isomer and S-(−)-isomer of the title compound.

Step B - Separation of Enantiomers:

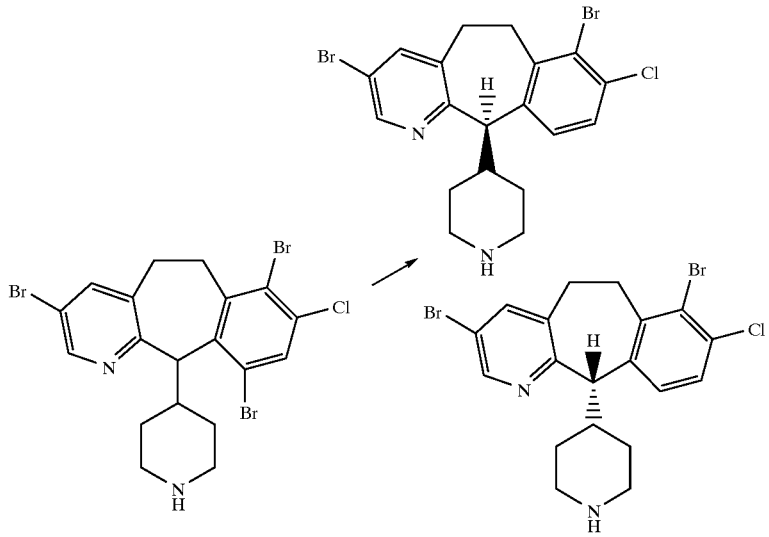

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. MH$^+$= 470.9, 472.8 (FAB); [a]$_D^{25}$=+43.5° (c=0.402, EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. MH$^+$= 470.9, 472.8 (FAB); [a]$_D^{25}$=−41.8° (c=0.328 EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

Physical chemical data for the R-(+)-isomer: $^{13}$C NMR (CDCl$_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3(C); 79.1 (CH); 52.3 (CH$_2$); 52.3 (CH); 45.6 (CH$_2$); 45.6 (CH$_2$); 30.0 (CH$_2$); 29.8 (CH$_2$). [a]$_D^{25}$=+25.8° (8.46 mg/2 mL MeOH).

Physical chemical data for the S-(−)-isomer: $^{13}$C NMR (CDCl$_3$): 155.9 (C); 146.4 (CH); 140.5 (CH); 140.2 (C); 136.2 (C); 135.3 (C); 133.3(C); 132.0 (CH); 129.9 (CH); 125.5 (CH); 119.2(C); 79.1 (CH); 52.5 (CH$_2$); 52.5 (CH); 45.7 (CH$_2$); 45.7 (CH$_2$); 30.0 (CH$_2$); 29.8 (CH$_2$). [a]$_D^{25}$=−27.9° (8.90 mg/2 mL MeOH).

PREPARATIVE EXAMPLE 11

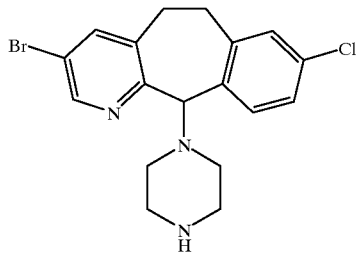

[racemic as well as R-(+)- and s-(-)-isomers]

EXAMPLE 1

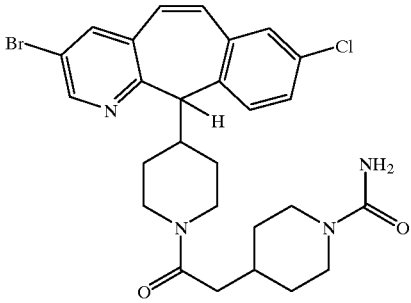

Step A:

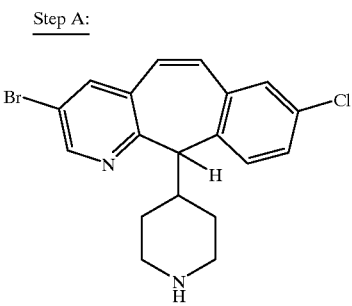

↓

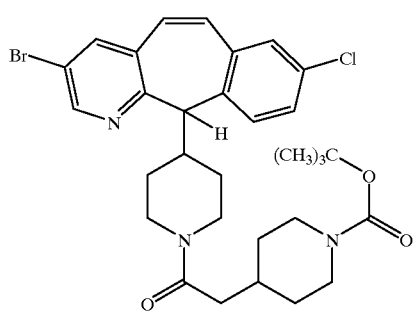

Dissolve 1.160 g (2.98 mmol) of the title compound from Preparative Example 3 in 20 mL of DMF, stir at room temperature, and add 0.3914 g (3.87 mmol) of 4-methylmorpholine, 0.7418 g (3.87 mmol) of DEC, 0.5229 g (3.87 mmol) of HOBT, and 0.8795 g (3.87 mmol) of 1-N-t-butoxycarbonyl-piperidinyl-4-acetic acid. Stir the mixture at room temperature for 2 days, then concentrate in vacuo to s residue and partition the residue between CH$_2$Cl$_2$ and water. Wash the organic phase successively with saturated NaHCO$_3$ (aqueous), 10% NaH$_2$PO$_4$ (aqueous) and brine. Dry the organic phase over MgSO$_4$, filter and concentrate in vacuo to a residue. Chromatograph the residue (silica gel, 2% MeOH/CH$_2$Cl$_2$+NH$_3$) to give 1.72 g of the product. m.p.=94.0–94.50° C., Mass Spec.: MH$^+$=616.3 elemental analysis: calculated-C, 60.54; H, 6.06; N, 6.83
found-C, 59.93; H, 6.62; N, 7.45

Step B:

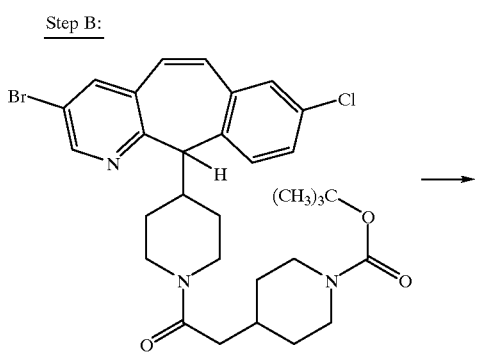

↓

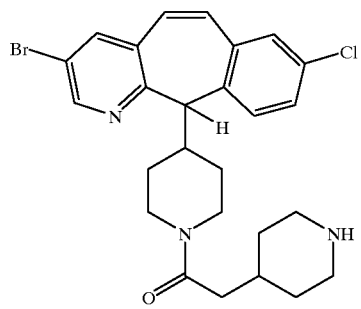

Combine 1.67 g (2.7 mmol) of the product of Step A and 20 mL of CH$_2$Cl$_2$ and stir at 0° C. Add 20 mL of TFA, stir the mixture for 2 hours, then basify the mixture with 1N NaOH (aqueous). Extract with CH$_2$Cl$_2$, dry the organic phase over MgSO$_4$, filter and concentrate in vacuo to give 1.16 g of the product. m.p. 140.2–140.8° C., Mass Spec.: MH$^+$=516.2.

Step C:

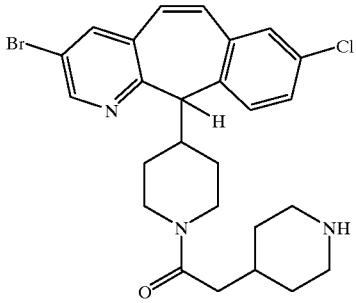

↓

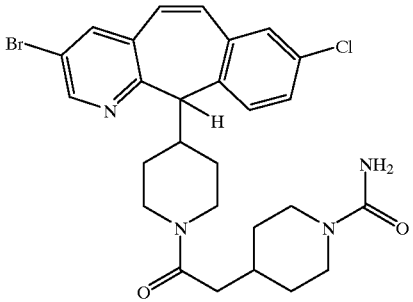

Combine 0.50 g of the product of Step B, 20 mL of CH$_2$Cl$_2$ and 4.5 equivalents of (CH$_3$)$_3$SiNCO and stir at room temperature for 3 hours. Extract the mixture with saturated NaHCO$_3$ (aqueous) and dry the organic phase over MgSO$_4$. Filter and concentrate in vacuo to give 0.8 g of the crude product. Chromatograph the crude product (silica gel, 5% MeOH/CH$_2$Cl$_2$+NH$_3$) to give 0.26 g of the product. m.p.=170.2–170.5° C., Mass Spec.: MH$^+$=559.1

EXAMPLE 2

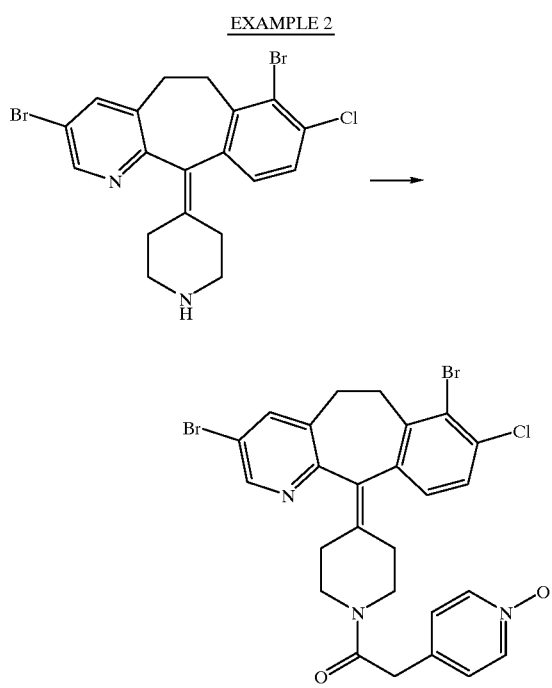

Combine 0.5 g (1.06 mmol) of the title compound of Preparative Example 4, 0.4 g (2.61 mmol) of the title compound of Preparative Example 1, 5 mL of dry DMF, and 0.5 mL (4.53 mmol) of 4-methylmorpholine, at 0° C., then add 0.6 g (3.12 mmol) of DEC and 0.4 g (2.96 mmol) of HOBT an stir the mixture overnight at 20° C. Concentrate in vacuo to a residue and extract the residue with $CH_2Cl_2$ (2×50 mL). Wash the extracts with 25 mL of water, dry over $MgSO_4$, then concentrate in vacuo to a residue and chromatograph (silica gel, 10% MeOH/EtOAc+2% $NH_4OH$ (aqueous)) to give 0.6 g (93.7% yield) of the title compound. Mass Spec.: $MH^+$=604.6 (FAB); partial $^1H$ NMR ($CDCl_3$, 300 MHz): 8.48 (s, 1H); 8.16 (d, 2H); 7.61 (s, 1H); 7.29 (m, 1H); 7.18 (d, 2H); 7.04 (d, 1H); 3.71 (s, 2H).

elemental analysis: calculated-C, 48.81; H, 4.10; N, 6.57
found-C, 49.10; H, 3.79; N, 6.74

EXAMPLE 3

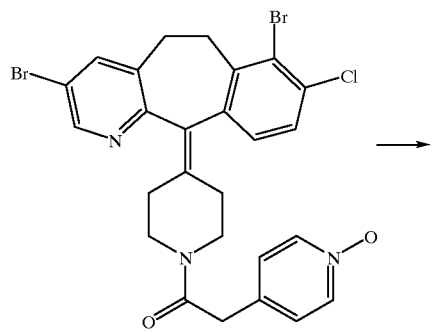

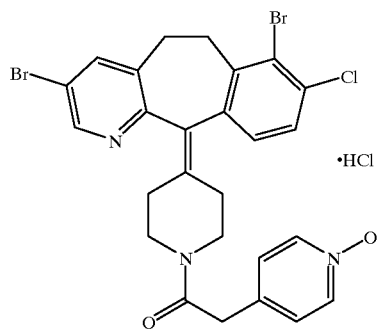

Dissolve 5.9 g (9.78 mmol) of the title compound of Example 2 in 300 mL of 1:5 $CH_2Cl_2$/EtOAc at 0° C. Slowly add (dropwise) 3 mL of 4N HCl (aqueous) and stir the mixture at 0° C. for 5 min. Add 200 mL of $Et_2O$, collect the resulting solids by filtration and wash the solids with 50 mL of $Et_2O$. Dry the solids at 20° C. and 0.2 mm Hg to give 5.9 g (96% yield) of the title compound. Mass Spec.: $MH^+$=604 (FAB). partial $^1H$ NMR (DMSO-$d_6$, 300 MHz): d 8.66 (d, 2H); 8.51 (s, 1H); 7.95 (s, 1H); 7.67 (d, 2H); 7.47 (m, 1H); 7.15 (m, 1H); 3.99 (s, 2H).

elemental analysis: calculated-C, 48.77; H, 3.62; N, 6.56
found-C, 48.34; H, 3.95; N, 6.84

EXAMPLE 4

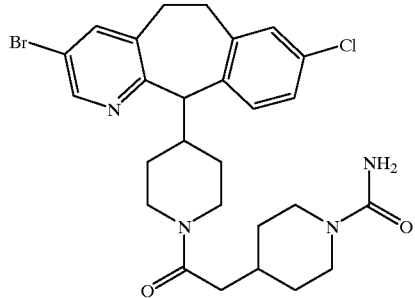

Step A:

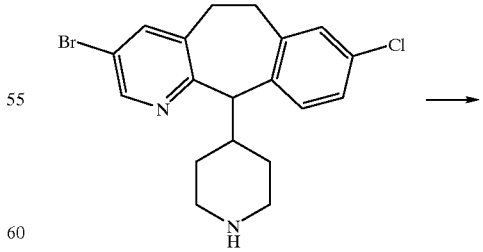

-continued

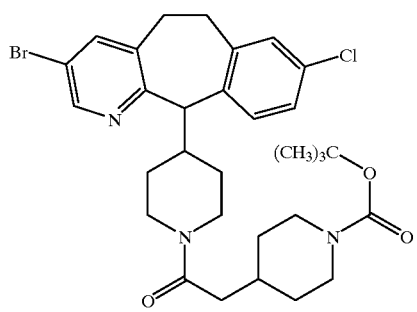

Combine 0.501 g (1.28 mmol) of the title compound of Preparative Example 5 and 20 mL of dry DMF, then add 0.405 g (1.664 mmol) of 1-N-t-butoxycarbonylpiperidinyl-4-acetic acid, 0.319 g (1.664 mmol) of DEC, 0.225 g (1.664 mmol) of HOBT, and 0.168 g (1.664 mmol) of 4-methylmorpholine and stir the mixture at room temperature overnight. Concentrate the mixture in vacuo to a residue, then partition the residue between 150 mL of $CH_2Cl_2$ and 150 mL of saturated $NaHCO_3$ (aqueous). Extract the aqueous phase with another 150 mL of $CH_2Cl_2$. Dry the organic phase over $MgSO_4$, and concentrate in vacuo to a residue. Chromatograph the residue (silica gel, 500 mL hexane, 1 L of 1% $MeOH/CH_2Cl_2$+0.1% $NH_4OH$ (aqueous), then 1 L of 2% $MeOH/CH_2Cl_2$+0.1% $NH_4OH$ (aqueous)) to give 0.575 g of the product.

m.p.=115°–125° C. Mass Spec.: $MH^+$=616.

Step B:

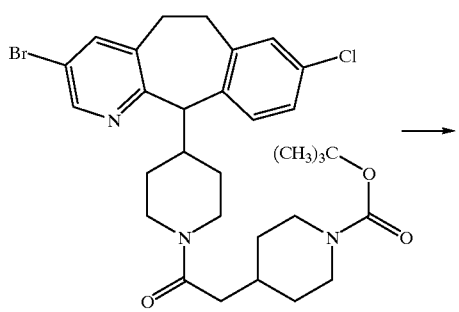

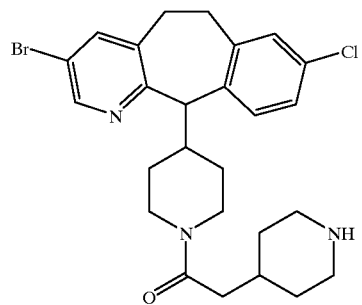

Combine 0.555 g (0.9 mmol) of the product of Step A and 15 mL of $CH_2Cl_2$ and cool the mixture to 0° C. Add 15 mL of TFA and stir at 0° C. for 2 hours. Concentrate in vacuo at 40–45° C. to a residue, then partition the residue between 150 mL of $CH_2Cl_2$ and 100 mL of saturated $NaHCO_3$ (aqueous). Extract the aqueous layer with 100 mL of $CH_2Cl_2$, combine the extracts and dry over $MgSO_4$. Concentrate in vacuo to give 0.47 g of the product.

m.p.=140°–150° C.; Mass Spec.: $MH^+$=516.

Step C:

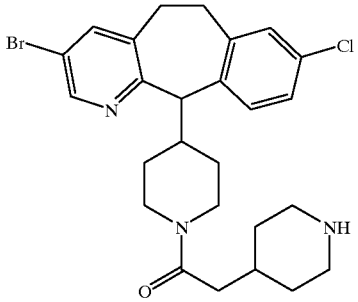

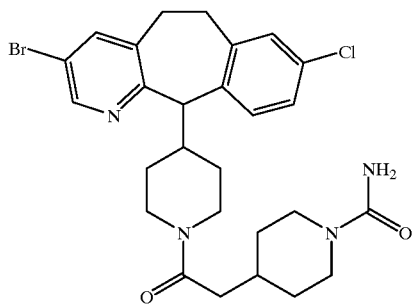

Combine 0.449 g (0.87 mmol) of the product of Step B, 20 mL of $CH_2Cl_2$ and 0.501 g (0.59 mmol) of $(CH_3)_3SiNCO$ and stir at room temperature overnight. Add 50–75 mL of saturated $NaHCO_3$ (aqueous) and stir for 0.5 hours. Dilute with $CH_2Cl_2$, separate the layers and extract the aqueous layer with 2×100 mL of $CH_2Cl_2$. Dry the combined $CH_2Cl_2$ extracts over $MgSO_4$ and concentrate in vacuo to a residue. Chromatograph the residue (silica gel, 500 mL $CH_2Cl_2$; 1 L of 1% $MeOH/CH_2Cl_2$+0.1% $NH_4OH$; 1 L of 2% $MeOH/CH_2Cl_2$+0.2% $NH_4OH$; then with 3% $MeOH/CH_2Cl_2$+0.3% $NH_4OH$) to give 0.33 g of the title compound.

m.p.=145°–155° C.; Mass Spec.: $MH^+$=559.

EXAMPLE 5

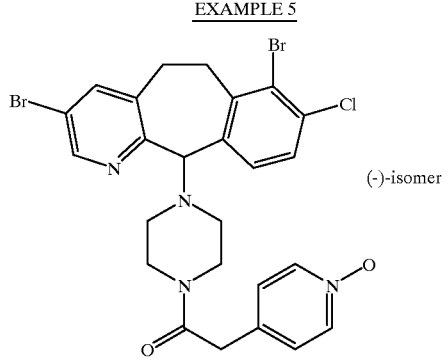

(−)-isomer

Combine 3.0 g (6.36 mmol) of the (−)-isomer the title compound from Preparative Example 6, Step D, and 70 mL of dry DMF. Add 3.84 mL (34.94 mmol) of N-methylmorpholine, 3.28 g (17.11 mmol) of DEC, 2.23 g (16.52 mmol) of HOBT and 2.09 (13.55 mmol) of 4-pyridylacetic acid N-oxide from Preparative Example 1 and stir the mixture at room temperature overnight. Concentrate in vacuo to remove the DMF, add 100 mL of saturated NaHCO$_3$ (aqueous) and 10 mL of CH$_2$Cl$_2$ and stir for 15 min. Extract the mixture with CH$_2$Cl$_2$ (2×500 mL), dry the extracts over MgSO$_4$ and concentrate in vacuo to a residue. Chromatograph the residue (500 g reverse phase C18 silica, gradient of 75%, 80%, then 85% MeOH/water+ 0.1% HOAC). Concentrate the desired fractions in vacuo to remove MeOH and add 50 mL of 1M NaOH (aqueous). Stir for 15 min., then extract with CH$_2$Cl$_2$ (2×500 mL). Dry the extract over MgSO$_4$ and concentrate in vacuo to give 3.4 g of the title compound. m.p.=148.9°–150.5° C.; $[a]_D^{25}$=−56.37° (9.4 mg/2mL MeOH); Mass Spec. MH$^+$=607.

The title compound of Example 5 can also be isolated as its HCl salt by treating a solution of the product in HCl and CH$_2$Cl$_2$ at room temperature, followed by concentration in vacuo to give the HCl salt. $[a]_D^{25}$=−31.9° (4.80 mg/2 mL MeOH+1 mL of water).

Using the (+)-isomer of the product of Preparative Example 6 and following essentially the same procedure as described above for Example 5, the analogous (+)-isomer (Example 5A), i.e., the enantiomer of the title compound of Example 5, is prepared. m.p.=149.0°–150.5° C.; Mass Spec.: MH$^+$=607; $[a]_D^{25}$=+67.1° (7.0 mg/2mL MeOH). The title compound of Example 5A can also be isolated as its HCl salt as described above for Example 5. m.p.=152.9° (dec.); $[a]_D^{25}$=+41.7° (2 mL MeOH+1 mL of water).

Using the racemic title compound of Preparative Example 6, Step C, and following essentially the same procedure as described above for Example 5, the racemate (Example 5B), is prepared. m.p.=84.3°–85.6° C.; Mass Spec.: MH$^+$=607.

EXAMPLE 6

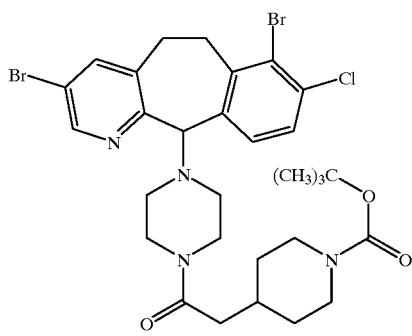

Step A:

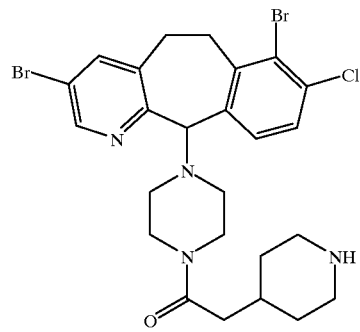

-continued

Combine 3.21 g (6.80 mmol) of the (−)-isomer product of Preparative Example 6 and 150 mL of anhydrous DMF. Add 2.15 g (8.8 mmol) of 1-N-t-butoxycarbonylpiperidinyl-4-acetic acid, 1.69 g (8.8 mmol) of DEC, 1.19 g (8.8 mmol) of HOBT and 0.97 mL (8.8 mmol) of N-methylmorpholine and stir the mixture at room temperature overnight. Concentrate in vacuo to remove the DMF and add 50 mL of saturated NaHCO$_3$ (aqueous). Extract with CH$_2$Cl$_2$ (2×250 mL), wash the extracts with 50 mL of brine and dry over MgSO$_4$. Concentrate in vacuo to a residue and chromatograph (silica gel, 2% MeOH/CH$_2$Cl$_2$+10% NH$_4$OH) to give 4.75 g of the product. m.p.=75.7°–78.5° C.; Mass Spec.: MH$^+$=697; $[a]_D^{25}$=−5.5° (6.6 mg/2 mL MeOH).

Step B:

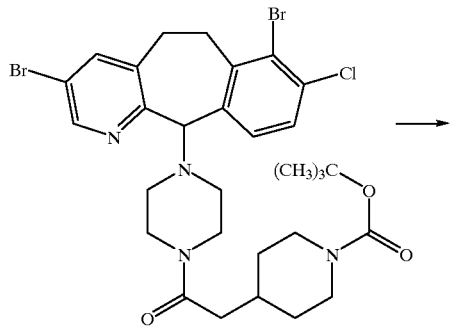

Combine 4.70 g (6.74 mmol) of the product of Step A and 30 mL of MeOH, then add 50 mL of 10% H$_2$SO4/dioxane in 10 mL aliquots over a 1 hr. period. Pour the mixture into 50 mL of water and add 15 mL of 50% NaOH (aqueous) to adjust to pH≈10–11. Filter to remove the resulting solids and extract the filtrate with CH$_2$Cl$_2$ (2×250 mL). Concentrate the aqueous layer in vacuo to remove the MeOH and extract again with 250 mL of CH$_2$Cl$_2$. Dry the combined extracts over MgSO$_4$ and concentrate in vacuo to give the product. m.p.=128.1°–131.5° C.; Mass Spec.: MH$^+$=597; [a]$_D^{25}$=−6.02° (9.3 mg/2 mL MeOH).

Step C:

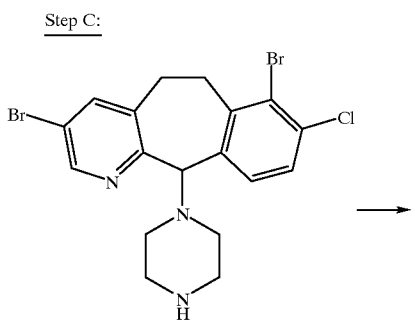

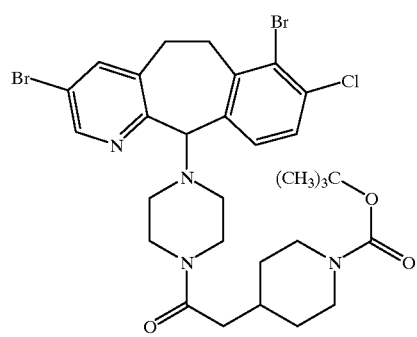

Combine 3.64 g (5.58 mmol) of the product of Step B and 30 mL of CH$_2$Cl$_2$, then add 6.29 mL (44.64 mmol) of (CH$_3$)$_3$SiNCO and stir the mixture for 2 days at room temperature. Add 25 mL of NaHCO$_3$ (aqueous), then extract with CH$_2$Cl$_2$ (2×250 mL). Wash the extracts with 25 mL of brine and dry over MgSO$_4$. Concentrate in vacuo to a residue and chromatograph (silica gel, gradient of 2.5%, 5.0%, then 7.5% MeOH/CH$_2$Cl$_2$+10% NH$_4$OH) to give the title compound. m.p.=150.5°–153.0° C.; Mass Spec.: MH$^+$=640; [a]$_D^{25}$=−61.4° (8.18 mg/2 mL MeOH).

EXAMPLE 7

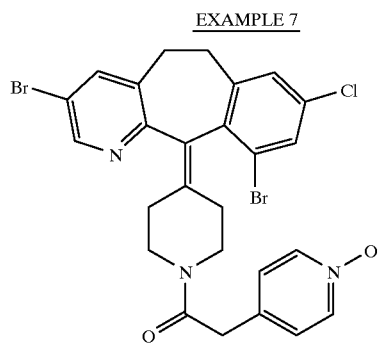

React the title compound of Preparative Example 7 and the title compound of Preparative Example 1 using substantially the same procedure as described for Example 2, to give 0.25 g of the title compound, which is a racemic mixture of atropisomers. Mass Spec.: MH$^+$=604. m.p.=167.2°–167.8° C.

The HCl salt of the title compound of Example 7 is prepared by stirring for 1 hr. with HClCH$_2$Cl$_2$, then concentrating in vacuo to give the salt.

EXAMPLES 7A & 7B

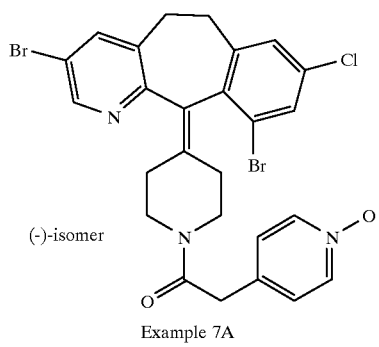

Example 7A

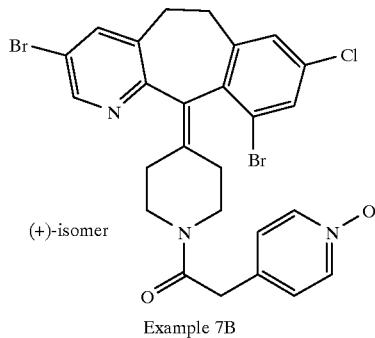

Example 7B

The title compound of Example 7 is a racemic mixture of atropisomers. Those atropisomers are separated by preparative chromatography (HPLC), using an Chiralpack AD column (5 cm×50 cm) and 40% i-PrOH/hexane+0.2% diethylamine as the mobile phase to give the (+)- and (−)-isomers, Examples 7B and 7A, respectively.

Physical chemical data for (−)-isomer, Example 7A: m.p.=114.2°–114.8° C.; [a]$_D^{25}$=−154.6° (8.73 mg/2 mL, MeOH).

Physical chemical data for (+)-isomer, Example 7B: m.p.=112.6°–113.5° C.; [a]$_D^{25}$=−159.7° (10.33 mg/2 mL, MeOH).

EXAMPLE 8

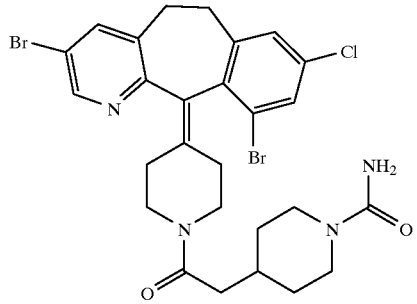

Step A:

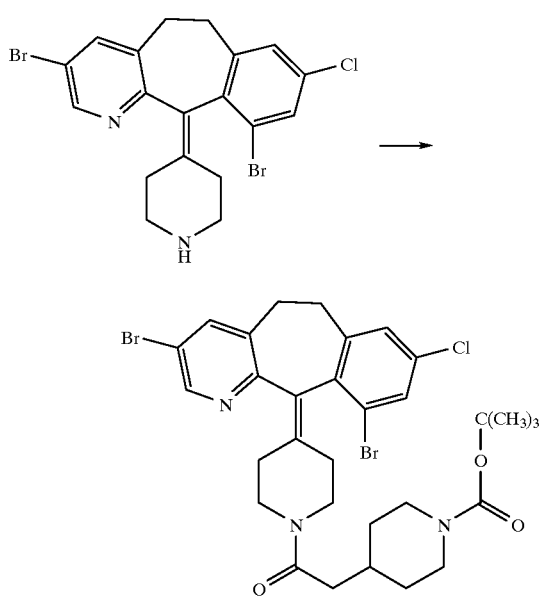

React 6.0 g (12.8 mmol) of the title compound of Example 8 and with 3.78 g (16.6 mmol) of 1-N-t-butoxycarbonyl-piperidinyl-4-acetic acid using substantially the same procedures as described for Example 6, Step A, to give 8.52 g of the product. Mass Spec.: MH$^+$=694.0 (FAB). $^1$H NMR (CDCl$_3$, 200 MHz): 8.5 (d, 1H); 7.5 (d, 2H); 7.2 (d, 1H); 4.15–3.9 (m, 3H); 3.8–3.6 (m, 1H); 3.5–3.15 (m, 3H); 2.9 (d, 2H); 2.8–2.5 (m, 4H); 2.4–1.8 (m, 6H); 1.8–1.6 (br d, 2H); 1.4 (s, 9H); 1.25–1.0 (m, 2H).

Step B:

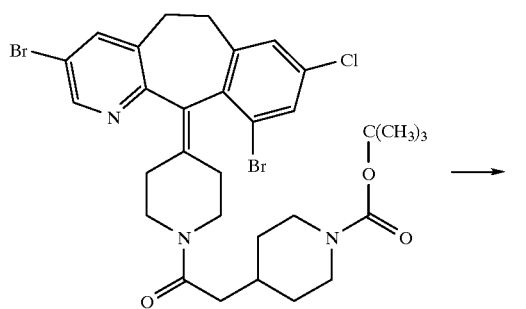

Combine 8.50 g of the product of Step A and 60 mL of CH$_2$Cl$_2$, then cool to 0° C. and add 55 mL of TFA. Stir the mixture for 3 h at 0° C., then add 500 mL of 1N NaOH (aqueous) followed by 30 mL of 50% NaOH (aqueous). Extract with CH$_2$Cl$_2$, dry over MgSO$_4$ and concentrate in vacuo to give 7.86 g of the product. Mass Spec.: M$^+$=593.9 (FAB). $^1$H NMR (CDCl$_3$, 200 MHz): 8.51 (d, 1H); 7.52 (d of d, 2H); 7.20 (d, 1H); 4.1–3.95 (m, 2H); 3.8–3.65 (m, 2H); 3.5–3.05 (m, 5H); 3.0–2.5 (m, 6H); 2.45–1.6 (m, 6H); 1.4–1.1 (m, 2H).

Step C:

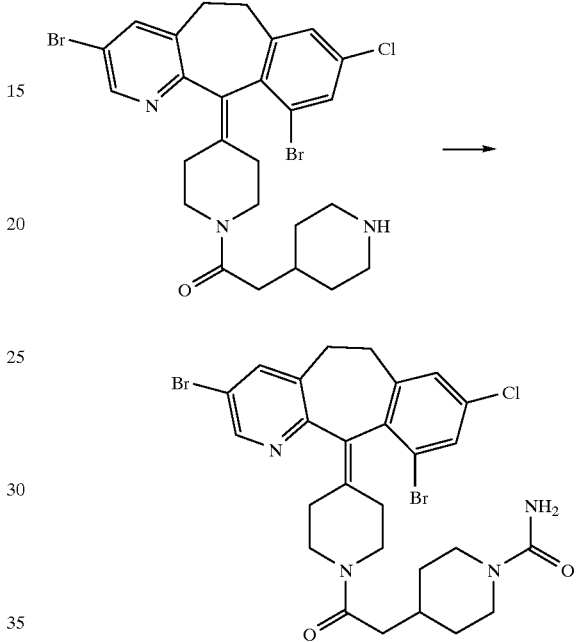

Treat 7.80 g (13.1 mmol) of the product of Step B with 12.1 g (105 mmol) of (CH$_3$)$_3$SiNCO using substantially the same procedure as described for Example 6, Step C, to give 5.50 g of the title compound, which is a racemic mixture of atropisomers. m.p.=163.6°–164.0° C. Mass spec.: M$^+$=636.9 (FAB). $^1$H NMR (CDCl$_3$, 200 MHz): 8.5 (d, 1H); 7.52 (d, 1H); 7.48 (d, 1H); 7.21 (d, 1H); 4.54, (s, 2H); 4.1–3.6 (m, 4H); 3.45–3.15 (m, 4H); 3.0–2.5 (m, 5H); 2.45–1.6 (m, 7H); 1.4–1.0, (m, 2H);

EXAMPLES 8A & 8B

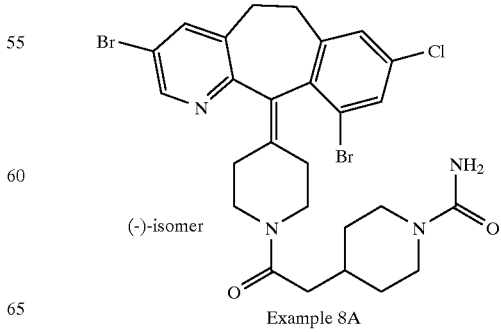

Example 8A

-continued

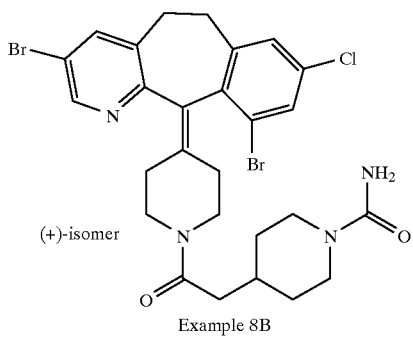

Example 8B

The title compound of Example 8 is a racemic mixture of atropisomers. Those atropisomers are separated by preparative chromatography (HPLC), using an Chiralpack AD column (5 cm×50 cm) and 20% i-PrOH/hexane+0.2% diethylamine as the mobile phase, at a flow rate of 100 mL/min., to give the (+)- and (−)-isomers, Examples 8B and 8A, respectively.

Physical chemical data for (−)-isomer, Example 8A: m.p.=142.9°–143.5° C.; $[a]_D^{25}$=−151.7° (11.06 mg/2 mL, MeOH).

Physical chemical data for (+)-isomer, Example 8B: m.p.=126.5°–127.0° C.; $[a]_D^{25}$=+145.6° (8.38 mg/2 mL, MeOH).

EXAMPLE 9

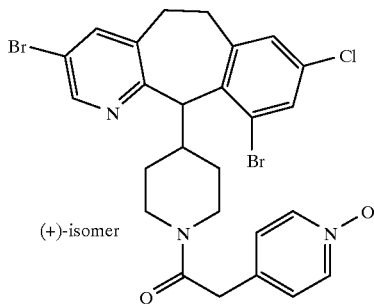

Combine 3.32 g of the (+)-isomer of the title compound of Preparative Example 8, Step B, 2.38 g of the title compound of Preparative Example 1, 1.92 g of HOBT, 2.70 g of DEC, 1.56 mL of N-methylmorpholine and 50 mL of dry DMF and stir at 25° C. for 24 hrs. Concentrate in vacuo, then dilute the residue with $CH_2Cl_2$. Wash with 1N NaOH (aqueous), then with saturated $Na_2HPO_4$ (aqueous) and dry over $MgSO_4$. Concentrate in vacuo to a residue and chromatograph (silica gel, 2% MeOH/$CH_2Cl_2$+$NH_4OH$) to give the crude product. Rechromatograph using 1% MeOH/$CH_2Cl_2$+$NH_4OH$ to give 3.82 g of the title compound.

The HCl salt of the title compound of Example 9 is prepared by dissolving of the title compound in $CH_2Cl_2$, adding 6M HCl (g) in $CH_2Cl_2$, then concentrating in vacuo to give the salt. m.p.=166.5° C.; $[a]_d^{25}$=+70.80° (MeOH).

EXAMPLES 9A & 9B

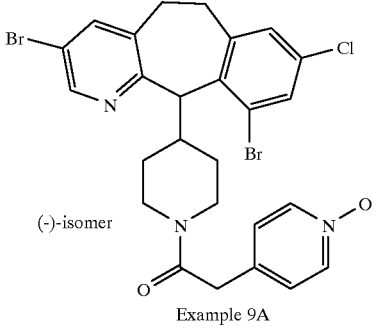

Example 9A

Example 9B

The (−)-isomer of the title compound of Preparative Example 8, Step B, (3.38 g) is reacted with 2.20 g of the title compound of Preparative Example 1, via substantially the same procedure as described for Example 9 to give 3.58 g of the title compound Example 9A.

The HCl salt of the title compound of Example 9A is prepared by dissolving of the title compound in $CH_2Cl_2$, adding 6M HCl (g) in $CH_2Cl_2$, then concentrating in vacuo to give the salt. m.p.=129° C.; $[a]_D^{25}$=−72.3° (MeOH).

The racemic title compound of Preparative Example 8, Step A, is reacted with the title compound of Preparative Example 1, via substantially the same procedure as described for Example 9 to give the title compound Example 9B. m.p.=145.0° C.

EXAMPLE 10

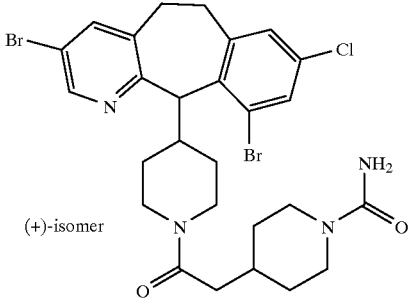

Step A:

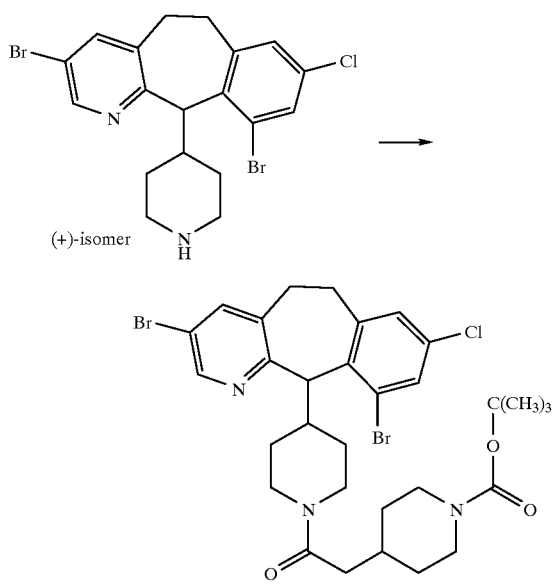

React 1.33 g of the (+)-isomer of the title compound of Preparative Example 8, Step B, with 1.37 g of 1-N-t-butoxy-carbonylpiperidinyl-4-acetic acid using substantially the same procedures as described for Example 6, Step A, to give 2.78 g of the product. Mass Spec.: MH$^+$=694.0 (FAB); $[a]_D^{25}$=+34.1° (mg/2 mL, MeOH).

Step B:

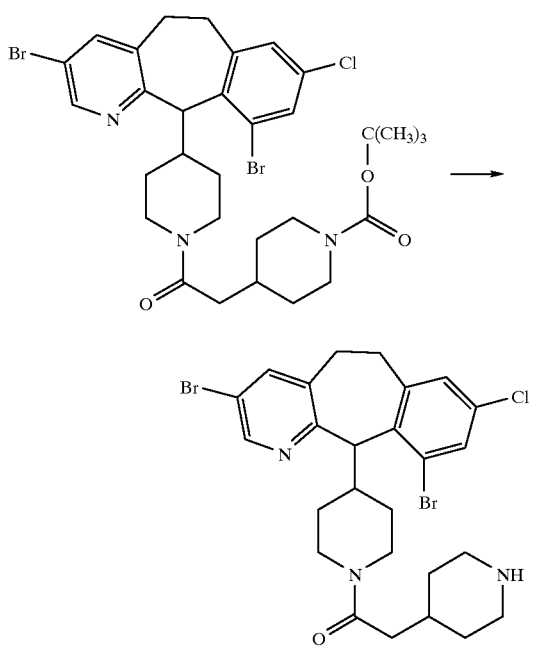

Treat 2.78 g of the product of Step A via substantially same procedure as described for Example 8, Step B, to give 1.72 9 of the product. m.p.=104.1° C.; Mass Spec.: M$^+$=597; $[a]_D^{25}$=+53.4° ( mg/2 mL, MeOH).

Step C:

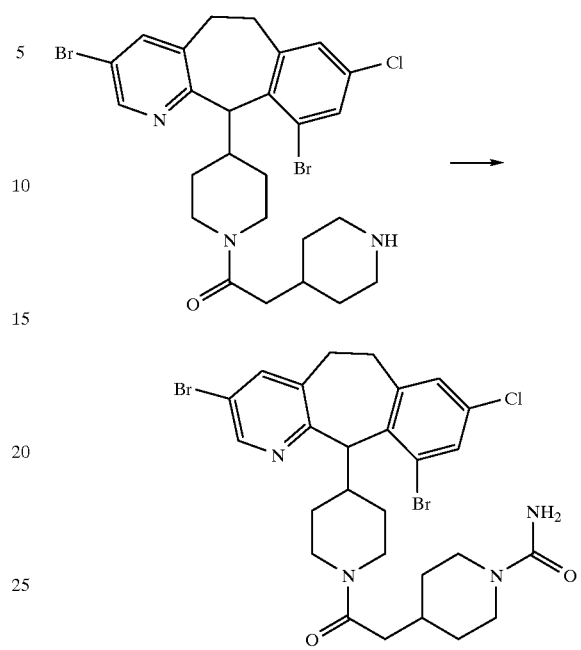

Treat 1.58 g of the product of Step B with 6 mL of (CH$_3$)$_3$SiNCO using substantially the same procedure as described for Example 6, Step C, to give 1.40 g of the title compound. m.p.=140° C; Mass spec.: M$^+$=639; $[a]_D^{25}$=+49.1° (mg/2 mL, MeOH).

EXAMPLES 10A & 10B

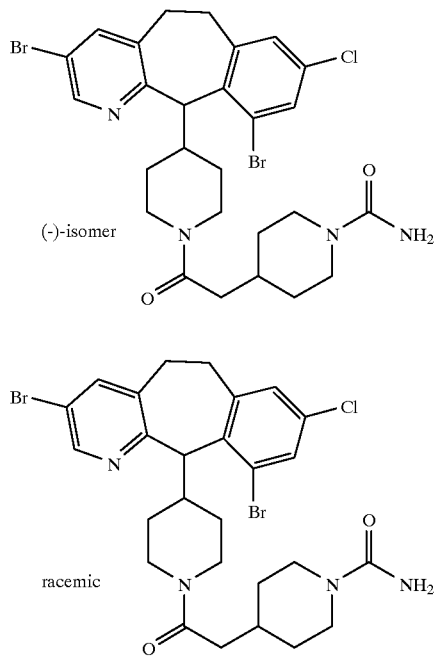

Example 10A  Example 10B

The (−)-isomer of the title compound of Preparative Example 8, Step B, (3.38 g) is converted to the title compound (Example 9A) via substantially the same procedure as described for Example 10, Steps A–C, to give the title compound Example 9A. m.p.=152° C; Mass spec.: M⁺=606; $[a]_D^{25}$=−62.5° (MeOH).

The racemic title compound of Preparative Example 8, Step A, is converted to the title compound (Example 9B) via substantially the same procedure as described for Example 10, Steps A–C to give the title compound Example 9B. m.p.=111.2° C. (dec).

Example 11

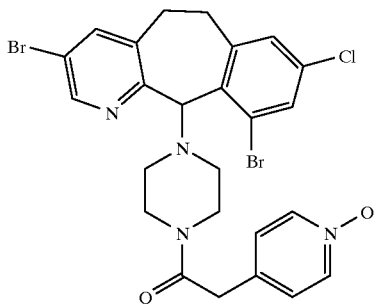

The title compound is prepared using the racemic title compound from Preparative Example 9, Step F, following substantially the same procedure as described for Example 2.

¹H NMR (CDCl₃, 400 MHz): 8.44 (d, 1H); 8.14 (d, 2H): 7.58 (d, 1H); 7.47 (d, 1H); 7.14 (m, 3H); 5.32 (s, 1H); 4.65–4.57 (m, 1H); 3.68 (s, 2H); 3.65–3.39 (m, 4H); 2.91–2.87 (m, 1H); 2.69–2.63 (m, 1H); 2.45–2.33 (m, 4H).

Examples 11A & 11B

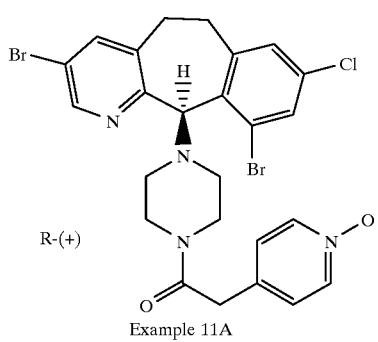

Example 11A

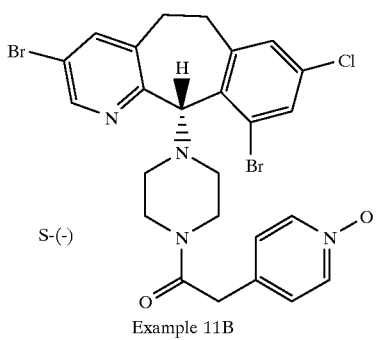

Example 11B

Using the R(+)- or S(−)-isomer of the title compound from Preparative Example 9, Step G, the R(+)-isomer (Example 11A) or the S-(−)-isomer (Example 11B) is prepared using substantially the same procedure as described for Example 2.

Physical chemical data for R-(+)-isomer, Example 11A: m.p. 167.0°–167.8° C.; $[a]_D^{25}$=+32.6° (MeOH); ¹H NMR (CDCl₃, 400 MHz): 8.44 (d, 1H); 8.14 (d, 2H): 7.58 (d, 1H); 7.47 (d, 1H); 7.14 (m, 3H); 5.32 (s, 1H); 4.65–4.57 (m, 1H); 3.68 (s, 2H); 3.65–3.39 (m, 4H); 2.91–2.87 (m, 1H); 2.69–2.63 (m,1H); 2.45–2.33 (m, 4H).

Physical chemical data for S-(−)-isomer, Example 11B: $[a]_D^{25}$=−38.2° (14.67 mg/2 mL, MeOH); ¹H NMR (CDCl₃, 400 MHz): 8.44 (d, 1H); 8.14 (d, 2H): 7.58 (d, 1H); 7.47 (d, 1H); 7.14 (m, 3H); 5.32 (s, 1H); 4.64–4.57 (m,1H); 3.67 (s, 2H); 3.70–3.34 (m, 4H); 2.95–2.87 (m, 1H); 2.69–2.63 (m, 1H); 2.45–2.31 (m, 4H).

Example 12

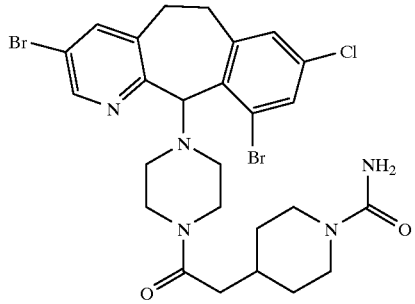

The title compound of this Example is prepared using the racemic title compound from Preparative Example 9, Step F. by following substantially the same procedures as described for Example 8, Steps A–C. This compound is a racemate.

EXAMPLES 12A & 12B

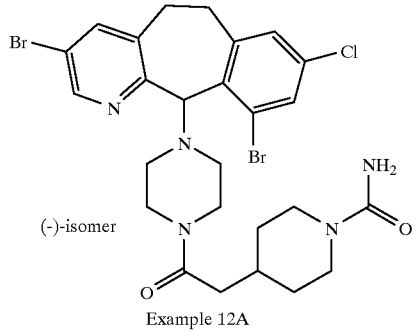

Example 12A

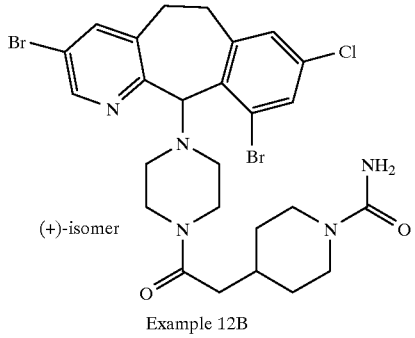

Example 12B

The title compound of Example 12 is a racemic mixture of enantiomers. Chromatograph 2.45 g of the compound of Example 12, using an Chiralpack AD column and 20% i-PrOH/ hexane+0.2% diethylamine as the mobile phase, at a flow rate of 100 mL/min., to give 0.970 g of the (+)-isomer and 0.982 g of the (−)-isomer, Examples 12B and 12A, respectively.

Physical chemical data for (−)-isomer, Example 12A: $^1$H NMR (CDCl$_3$, 200 MHz): 8.43 (d, 1H); 7.58 (d, 1H); 7.48 (d, 1H); 7.14 (d, 1H); 5.32 (s, 1H); 4.5–4.75 (m, 1H); 4.4 (s, 2H); 3.9 (d, 2H); 3.2–3.7 (m, 5H); 2.52–3.05 (m, 4H); 1.85–2.5 (m, 6H); 1.5–1.85 (m, 4H); 1.0–1.4 (m, 1H). $[a]_D^{25}=-31.2°$ (MeOH).

Physical chemical data for (+)-isomer, Example 12B: $^1$H NMR (CDCl$_3$, 200 MHz): 8.43 (d, 1H); 7.58 (d, 1H); 7.48 (d, 1H); 7.14 (d, 1H); 5.32 (s, 1H); 4.5–4.75 (m, 1H); 4.4 (s, 2H); 3.9 (d, 2H); 3.2–3.7 (m, 5H); 2.52–3.05 (m, 4H); 1.85–2.5 (m, 6H); 1.5–1.85 (m, 4H); 1.0–1.4 (m, 1H). $[a]_D^{25}=+29.8°$ (MeOH).

EXAMPLE 13

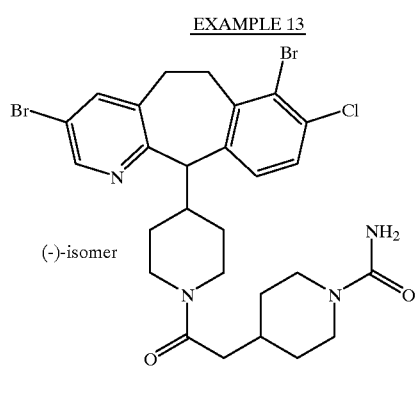

Step A:

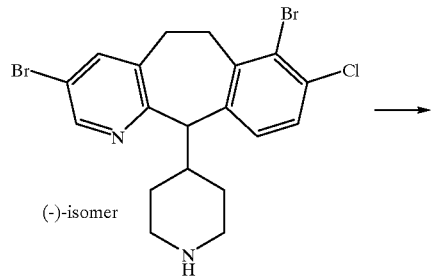

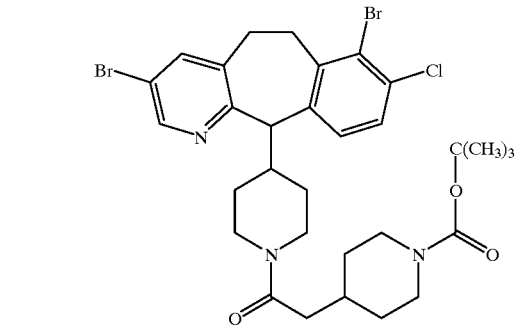

React 1.35 g of the (−)-isomer of the title compound of Preparative Example 10, Step B, with 1.4 g of 1-N-t-butoxy-carbonylpiperidinyl-4-acetic acid following substantially the same procedures as described for Example 6, Step A, to give 2.0 g of the product. Mass Spec.: MH$^+$=696 (FAB). partial $^1$H NMR (CDCl$_3$, 300 MHz): 8.38 (s, 1H); 7.60 (s, 1H); 7.25 (d, 1H); 7.05 (m, 1H); 1.45 (s, 9H).

Step B:

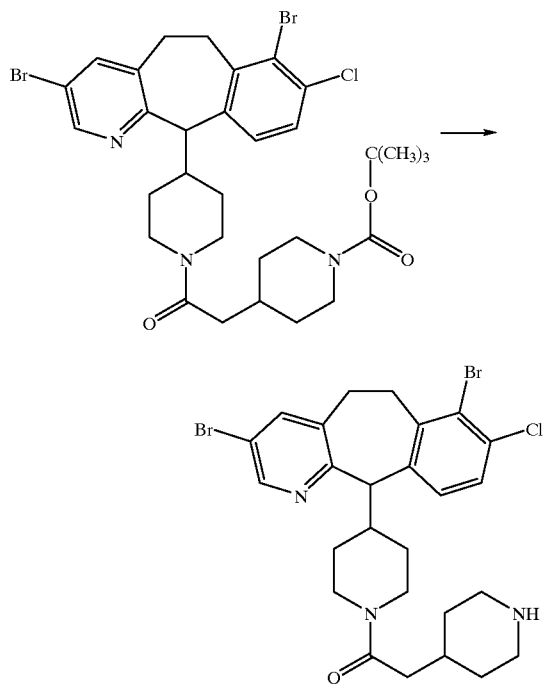

Treat 1.95 g of the product of Step A via substantially the same procedure as described for Example 8, Step B, to give 1.63 g of the product. Mass Spec. MH$^+$=596 (FAB). partial $^1$H NMR (CDCl$_3$, 300 MHz): 8.38 (s, 1H); 7.60 (s, 1H); 7.25 (d, 1H); 7.03 (m, 1H); 4.64 (d, 1H); 3.90 (m, 2H).

Step C:

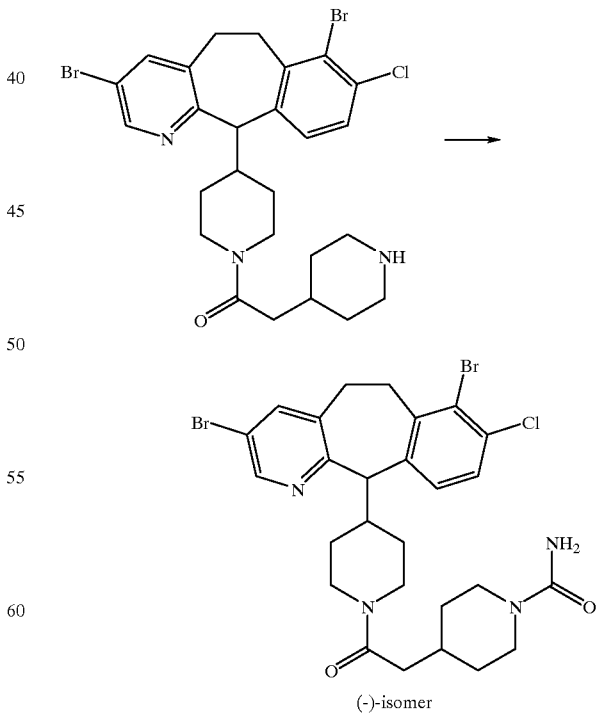

Treat 1.6 g of the product of Step B with 1.3 mL of (CH$_3$)$_3$SiNCO using substantially the same procedure as described for Example 6, Step C, to give 1.27 g of the title compound. Mass spec.: M$^{+=}$639 (FAB); $[a]_D^{25}$=−33.1° (c=0.58, EtOH). partial $^1$H NMR (CDCl$_3$, 400 MHz): 8.38 (s, 1H); 7.59 (s, 1H); 7.25 (d, 1H); 7.04 (m, 1H); 4.60 (d, 1H); 4.41 (s, 2H).

EXAMPLES 13A & 13B

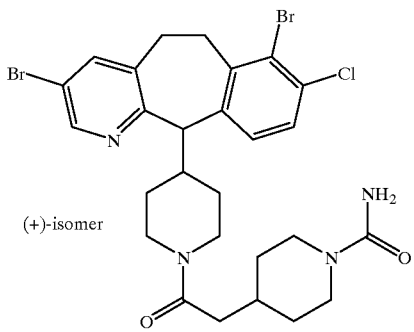

(+)-isomer

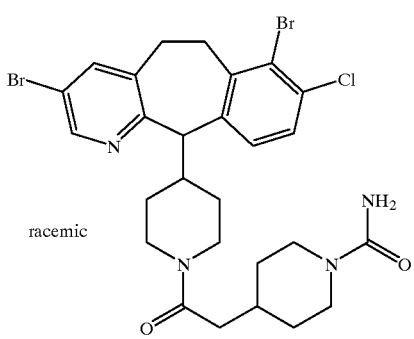

racemic

Example 13A                Example 13B

The (+)-isomer of the title compound from Preparative Example 10, Step B, (2.1 g) is converted to the title compound via substantially the same procedure as described for Example 10, Steps A–C, to give the title compound, Example 13A. Mass spec.: MH$^+$=638.9; $[a]_D^{25}$=+32.4° (c=0.57, EtOH). partial $^1$H NMR (CDCl$_3$, 400 MHz): 8.39 (s, 1H); 7.59 (s, 1H); 7.25 (d, 1H); 7.04 (m, 1H); 4.60 (d, 1H); 4.41 (s, 2H). partial $^1$H NMR (DMSO-d$_6$, 400 MHz): 8.42 (s, 1H); 7.88 (s, 1H); 7.41 (d, 1H); 7.29 (m,1H); 5.85 (s, 2H); 4.20 (d, 1H).

The racemic title compound from Preparative Example 10, Step A, is converted to the racemic title compound, Example 13B, in an analogous manner. partial $^1$H NMR (CDCl$_3$, 400 MHz): 8.38 (s, 1H); 7.59 (s,1H); 7.25 (d,1H); 7.04 (m,1H); 4.60 (d,1H); 4.41 (s, 2H). partial $^1$H NMR (DMSO-d$_6$, 400 MHz): 8.42 (s,1H); 7.88 (s,1H); 7.41 (d,1H); 7.29 (d,1H); 5.85 (s, 2H); 4.20 (d,1H).

EXAMPLE 14

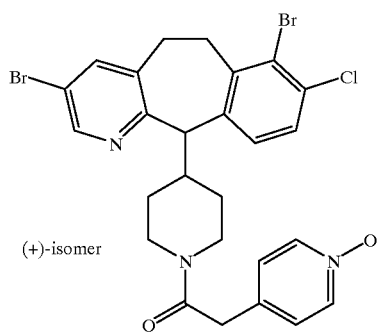

(+)-isomer

React 2.6 g of the (+)-isomer of the title compound of Preparative Example 10, Step B, and 1.68 g of the title compound of Preparative Example 1 following substantially the same procedure as described for Example 9 to give 2.10 g of the title compound. Mass spec.: MH$^+$=606 (FAB); $[a]_D^{25}$=+34.1° (10.98 mg/2 mL, EtOH). partial $^1$H NMR (CDCl$_3$, 400 MHz): 8.38 (s, 1H); 8.15 (d, 2H); 7.58 (s, 1H); 7.26 (d, 1H); 7.15 (d, 2H); 7.03 (d, 1H); 4.57 (d, 1H).

To prepared the HCl salt of the title compound of Example 14 dissolve 700 mg of the title compound in 4 mL of CH$_2$Cl$_2$, add 4 mL of Et$_2$O, cool to 0° C. and slowly add (dropwise) 1 mL of HCl (g) in dioxane. Add 2 mL of Et$_2$O and stir at 0° C. for 7 min. Dilute with 30 mL of Et$_2$O, filter to collect the solid product and wash with 30 mL of Et$_2$O. Dry the solids in vacuo to give 0.836 g of the HCl salt of Example 14. $[a]_D^{25}$=+64.8° (9.94 mg/2 mL, EtOH).

EXAMPLE 14A & 14B

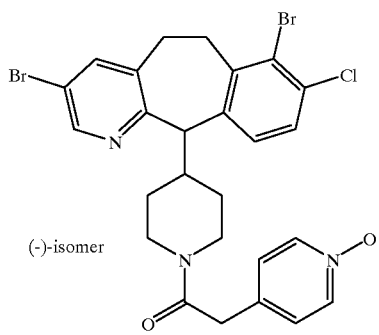

(−)-isomer

Example 14A

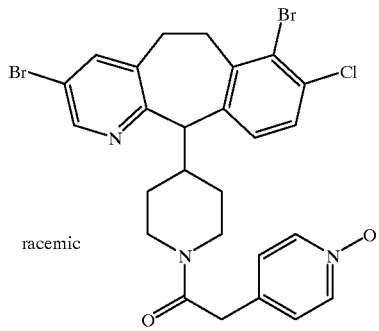

racemic

Example 14B

The (−)-isomer of the title compound of Preparative Example 10, Step B, (0.60 g) is reacted with 0.39 g of the title compound of Preparative Example 1, via substantially the same procedure as described for Example 9 to give 0.705 g of the title compound. Mass spec.: MH$^+$=604 (FAB); [a]$_D^{25}$=−41.8° (EtOH). partial $^1$H NMR (CDCl$_3$, 300 MHz): 8.38 (s, 1H); 8.15 (d, 2H); 7.58 (s, 1H); 7.26 (d, 1H); 7.15 (d, 2H); 7.03 (d,1H); 4.57 (d,1H).

The HCl salt of the title compound of Example 14A is prepared via substantially the same procedure as described for Example 14. [a]$_D^{25}$=−63.2° (EtOH).

The racemic title compound of Preparative Example 10, Step A, is converted to the racemic title compound of Example 14B following substantially the same procedure as described for Example 9. partial $^1$H NMR (CDCl$_3$, 400 MHz): 8.38 (s, 1H); 8.15 (d, 2H); 7.58 (s, 1H); 7.26 (d, 1H); 7.15 (d, 2H); 7.03 (d, 1H); 4.57 (d, 1H). partial $^1$H NMR (DMSO-d$_6$, 400 MHz): 8.77 (d, 2H); 8.47 (s, 1H); 7.95 (s, 1H); 7.74 (d, 2H); 7.43 (m, 1H); 7.27 (d, 1H); 4.35 (d, 1H).

EXAMPLE 15

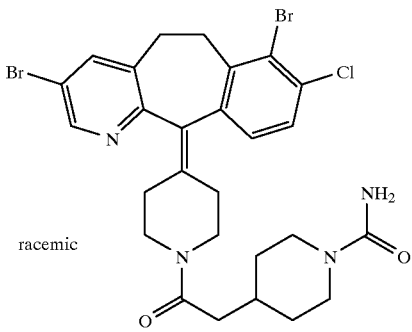

racemic

The title compound of Preparative Example 4 is reacted via substantially the same methods as described for Example 8, Steps A–C to give the title compound, which is a racemate. Mass Spec.: MH$^+$=637 (FAB). partial $^1$H NMR (CDCl$_3$): 8.45 (s, 1H); 7.60 (s, 1H); 7.35 (d, 1H); 7.05 (d, 1H); 4.45 (s, 1H).

Example 16A & 16B

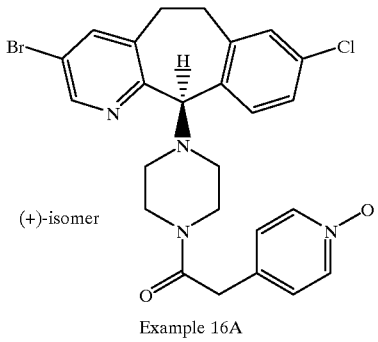

(+)-isomer

Example 16A

-continued

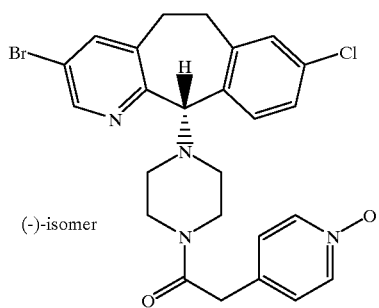

(−)-isomer

Example 16B

The R-(+)-isomer or the S-(−) isomer of the title compound of Preparative Example 11 is treated via substantially the same procedure as described for Example 2 to give the R-(+)-isomer of the title compound or the S-(−)-isomer of the title compound, Examples 16A and 16B, respectively.

Physical chemical data for the R-(+)-isomer: $^{13}$C NMR (CDCl$_3$): 166.5 (C); 154.8 (C); 146.6 (CH); 140.8 (CH); 140.4 (C); 138.5 (CH); 138.5 (CH); 136.3 (C); 134.6 (C); 133.8 (C); 133.6 (C); 132.0 (CH); 130.0 (CH); 126.3 (CH); 126.3 (CH); 125.8 (CH); 119.6 (C); 78.4 (CH); 51.1 (CH$_2$); 50.6 (CH$_2$); 45.4 (CH); 41.5 (CH$_2$); 38.0 (CH$_2$); 30.1 (CH$_2$); 30.0 (CH$_2$). [a]$_D^{25}$=+30.7° (10.35 mg/2 mL MeOH).

Physical chemical data for the S-(−)-isomer: $^{13}$C NMR (CDCl$_3$): 166.5 (C); 154.8 (C); 146.6 (CH); 140.8 (CH); 140.4 (C); 138.5 (CH); 138.5 (CH); 136.3 (C); 134.6 (C); 133.8 (C); 133.6 (C); 132.0 (CH); 130.0 (CH); 126.3 (CH); 126.3 (CH); 125.8 (CH); 119.6 (C); 78.4 (CH); 51.1 (CH$_2$); 50.6 (CH$_2$); 45.4 (CH); 41.5 (CH$_2$); 38.0 (CH$_2$); 30.1 (CH$_2$); 29.9 (CH$_2$). [a]$_D^{25}$=−30.9° (9.70 mg/2 mL MeOH).

Example 17 & 17A

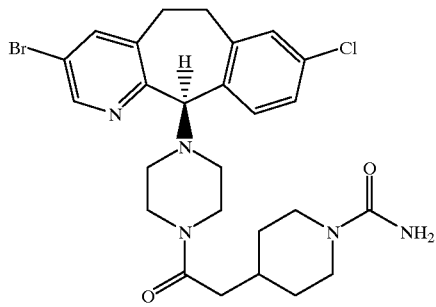

-continued

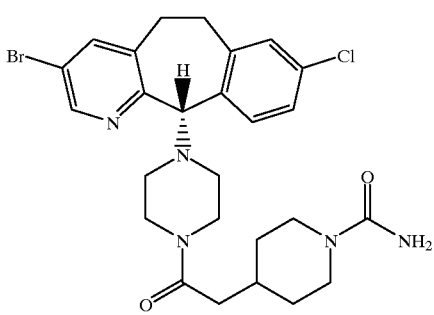

Example 17

-continued

Step A:

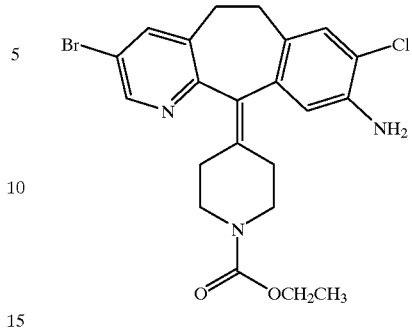

Treat the (+)-isomer or the (−)-isomer of the title compound of Preparative Example 11 via substantially the same procedure as described for Example 1, Steps A–C to give the R-(+)-isomer of the title compound or the S-(−)-isomer of the title compound, Examples 17 and 17A, respectively.

Physical chemical data for the R-(+)-isomer: $^{13}$C NMR (CDCl$_3$): 169.3 (C); 157.5 (C); 155.0 (C); 146.6 (CH); 140.8 (CH); 140.4 (C); 136.3 (C); 134.8 (C); 133.7 (C); 132.0 (CH); 130.0 (CH); 125.8 (CH); 119.6 (C); 78.5 (CH); 51.4 (CH$_2$); 50.9 (CH$_2$); 45.2 (CH); 43.9 (CH$_2$); 43.9 (CH$_2$); 41.1 (CH$_2$); 38.8 (CH$_2$); 32.5 (CH); 31.5 (CH$_2$); 31.5 (CH$_2$); 30.1 (CH$_2$); 30.0 (CH$_2$). $[a]_D^{25}$=+28.7° (10.1 mg/2 mL MeOH).

Physical chemical data for the S-(−)-isomer: $^{13}$C NMR (CDCl3): 169.3 (C); 157.6 (C); 155.0 (C); 146.6 (CH); 140.8 (CH); 140.4 (C); 136.3 (C); 134.8 (C); 133.7 (C); 132.0 (CH); 130.0 (CH); 125.8 (CH); 119.6 (C); 78.5 (CH); 51.4 (CH$_2$); 50.9 (CH$_2$); 45.2 (CH); 43.9 (CH$_2$); 43.9 (CH$_2$); 41.1 (CH$_2$); 38.8 (CH$_2$); 32.5 (CH); 31.5 (CH$_2$); 31.5 (CH$_2$); 30.1 (CH$_2$); 30.0 (CH$_2$). $[a]_D^{25}$=−28.50 (10.1 mg/2 mL MeOH).

Dissolve 9.90 g (18.9 mmol) of the product of Preparative Example 7, Step B, in 150 mL CH$_2$Cl$_2$ and 200 mL of CH$_3$CN and heat to 60° C. Add 2.77 g (20.8 mmol) N-chlorosuccinimide and heat to reflux for 3 h., monitoring the reaction by TCL (30%EtOAc/H$_2$O). Add an additional 2.35 g (10.4 mmol) of N-chlorosuccinimide and reflux an additional 45 min. Cool the reaction mixture to room temperature and extract with 1N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C.

EXAMPLE 18

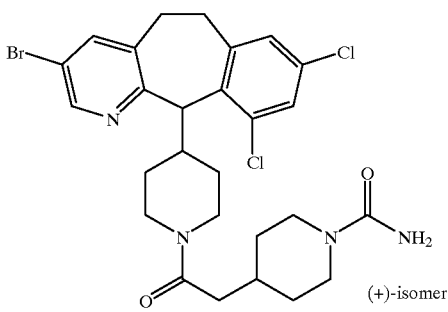

(+)-isomer

Step B:

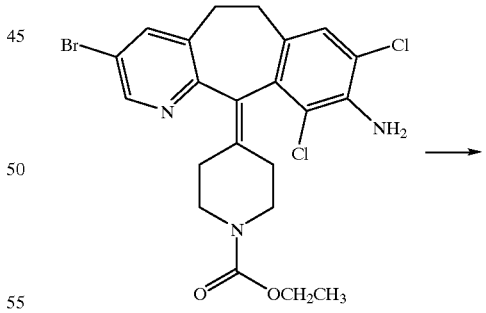

-continued

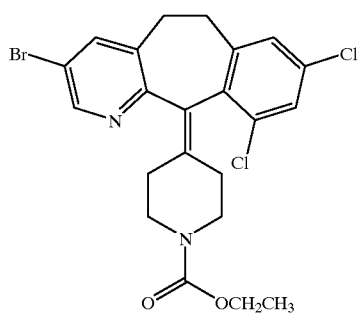

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basify with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/hexane) to obtain 3.98 g of product. Mass spec.: MH$^+$= 497.2.

Step C:

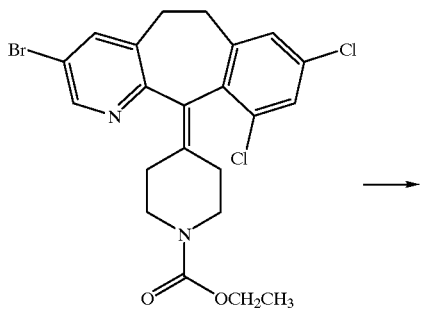

Dissolve 3.9 g of the product of Step B in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product. Mass spec.: MH$^+$=424.9.

Step D:

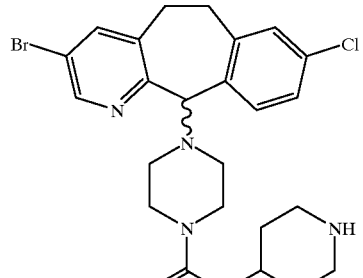

Using a procedure similar to that described in Preparative Example 8, obtain 1.73 g of the desired product, m.p. 169.6–170.1° C.; $[a]_D^{25}$=+48.2° (c=1, MeOH).

Step E

Use a procedure similar to that of Example 4 with the product of Step D as the starting material to obtain the title compound. M.p. 152.3–153.3° C.; $[a]_D^{25}$=+53.0° (c=1, MeOH).

EXAMPLE 19

4-[2-[4-(3-BROMO-8-CHLORO-6,11-DIHYDRO-5H-BENZO[5,6]CYCLOHEPTA[1,2-b]PYRIDIN-11-YL)-1-PIPERAZINYL]-2-OXOETHYL]-1-PIPERIDINE CARBOXAMIDE

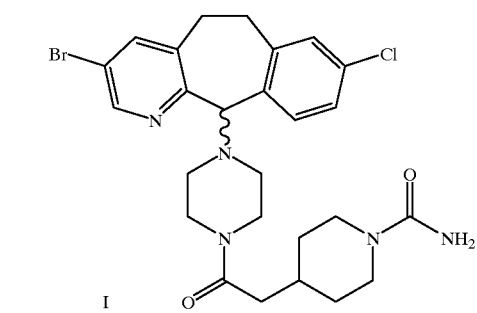

Procedure (i):

1-(3-Bromo-8-chloro-6,11-dihydro-5H-benzo[5,6]cyclohepta[1,2-b]pyridin-11-yl)-4-[(4-piperidinyl)) acetyl] piperazine (1 equivalent) (0.3g) and urea (Aldrich 99%) (10 equivalents) (0.3479 g) were slurried in distilled water (3 ml) and the heterogeneous mixture was heated under reflux at 100° C. for 66 h with stirring. The mixture was dissolved in methanol/dichloromethane and then evaporated to dryness. The product was chromatographed on a silica gel column (15×2.5 cm) using 3% (10% concentrated ammonium hydroxide in methanol)-dichloromethane as the eluant to give the title compound (0.2863 g.; 88%), FABMS: m/z 562.1 (MH$^+$).

| | | $d_C$ (CDCl$_3$) |
|---|---|---|
| Tricyclic | CH$_2$: | 30.5, 30.6 |
| | CH: | 147.1, 141.4, 132.5, 126.3, 130.6, 79.1 |
| | C: | 120.1, 140.9, 134.3, 135.2, 136.9, 155.4 |
| Piperazine | CH$_2$: | 41.6, 45.7, 51.5, 51.9 |
| Piperazine | CH$_2$: | 44.4, 44.5, 32.1, 39.3 |
| N-substitiuent | CH: | 33.0 |
| | C: | 169.8, 158.1 |

Procedure (ii):

1-(3-Bromo-8-chloro-6,11-dihydro-5H-benzo[5,6]cyclohepta[1,2-b]pyridin-11-yl)-4-[(4-piperidinyl)) acetyl] piperazine (1 equivalent) (0.3 g) and urea (Aldrich 99%) (4 equivalents) (0.1392 g) were slurried in distilled water (12 ml) and the mixture was heated under reflux at 100° C. for 3 h with stirring. The mixture was dissolved in methanol/dichloromethane and then evaporated to dryness. The product was chromatographed on a silica gel column (15×2.5cm) using 3% increasing to 7% (10% concentrated ammonium hydroxide in methanol)-dichloromethane as the eluant to give the title compound (0.1486 g.; 46%), which was identical to that prepared in Procedure (i) above.

Procedure (iii):

1-(3-Bromo-8-chloro-6,11-dihydro-5H-benzo[5,6]cyclohepta[1,2-b]pyridin-11-yl)-4-[(4-piperidinyl) acetyl] piperazine (1 equivalent) (0.3 g) and urea (Aldrich 99%) (4 equivalents) (0.1392 g) were slurried in distilled water (3 ml) and the mixture was heated under reflux at 100° C. for 18 h with stirring. The mixture was dissolved in methanol/dichloromethane and then evaporated to dryness. The product was chromatographed on a silica gel column (15×2.5cm) using 3% increasing to 7% (10% concentrated ammonium hydroxide in methanol)-dichloromethane as the eluant to give the title compound (0.2163 g.; 67%), which was identical to that prepared in Procedures (i) and (ii) above.

EXAMPLE 20

(+)-4-[2-[4-(8-CHLORO-3,10-DIBROMO-6,11-DIHYDRO-5H-BENZO[5,6]CYCLOHEPTA[1,2-b]PYRIDIN-11(R)-YL)-1-PIPERIDINYL]-2-OXOETHYL]-1-PIPERIDINECARBOXAMIDE

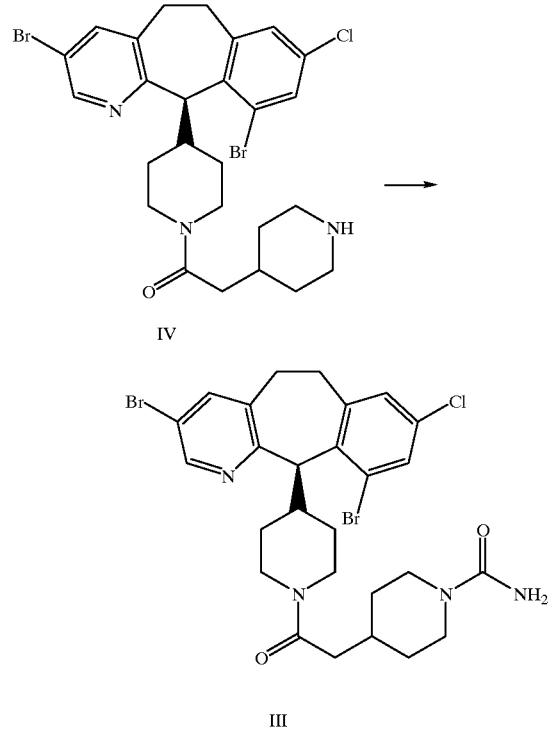

(+)-4-(8-Chloro-3,10-dibromo-6,11-dihydro-5H-benzo[5,6]cyclohepta[1,2-b]pyridin-11(R)-yl)-1-(4-piperidinylacetyl)) piperidine (1 equivalent) (0.060 g) and urea (Aldrich 99%) (10 equivalents) (0.065 g) were slurried in distilled water (1 ml) and the mixture was heated under reflux at 100° C. for 68 h with stirring, the volume being maintained at 1 ml throughout the reaction by the addition of water as needed. The mixture was dissolved in methanol/dichloromethane and then evaporated to dryness. The product was chromatographed on a silica gel column (15×1 cm) using 3% (10% concentrated ammonium hydroxide in methanol)-dichloromethane as the eluant to give the title compound (0.0632 g; 98%), FABMS: m/z 639.4 (MH$^+$).

| | | $d_C$ (CDCl$_3$) |
|---|---|---|
| Tricyclic | CH$_2$: | 30.2, 30.2 |
| | CH: | 147.5/147.3, 141.5/1.41.7, 131.1/131.2, 129.2/129.3, 58.1 |
| | C: | 119.0, 142.6/142.7, 135.2/135.4, 133.2/133.3, 127.2/127.3, 137.0/137.3, 154.7/154.8 |
| Piperidine | CH$_2$: | 45.9/45.8, 42.0/41.8, 31.2/31.3, 31.9 |
| | CH: | 42.0/42.2 |
| Piperidine | CH$_2$: | 44.4/44.6, 44.4/44.6, 32.1/32.2, 32.1/32.2, 39.4 |
| N-substituent | CH: | 33.0 |
| | C: | 169.7, 158.0 |

We claim:

1. A process for producing the compounds of the formula (1.0):

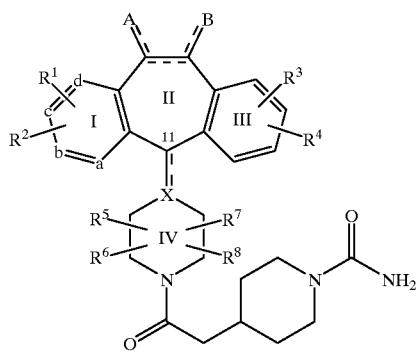
(1.0)

wherein all substituents are as described below,
which comprises reacting a water insoluble compound of the formula (1.0)'

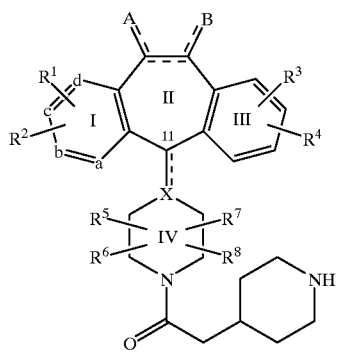
(1.0)' with an excess of urea in water;
wherein X is N, CH, or, C when a double bond is present at the C-11 position;
one of a, b, c and d represents N or NR$^9$ wherein R$^9$ is O$^-$, —CH$_3$ or —(CH$_2$)$_n$CO$_2$H wherein n is 1 to 3, and the remaining a, b, c and d groups represent CR$^1$ or CR$^2$; or
each of a, b, c, and d are independently selected from CR$^1$ or CR$^2$;
each R$^1$ and each R$^2$ is independently selected from H, halo, —CF$_3$, —OR$^{10}$, —COR$^{10}$, —SR$^{10}$, —S(O)$_t$R$^{11}$ (wherein t is 0, 1 or 2, —SCN, —N(R$^{10}$)$_2$, —NR$^{10}$R$^{11}$, —NO$_2$, —OC(O)R$^{10}$, —CO$_2$R$^{10}$, —OCO$_2$R$^{11}$, —CN, —NHC(O)R$^{10}$, —NHSO$_2$R$^{10}$, —CONHR$^{10}$, —CONHCH$_2$CH$_2$OH, —NR$^{10}$COOR$^{11}$,

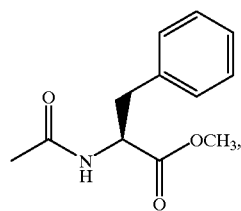

—SR$^{11}$C(O)OR$^{11}$, —SR$^{11}$N(R$^{12}$)$_2$ wherein each R$^{12}$ is independently selected from H and —C(O)OR$^{11}$, benzotriazol-1-yloxy, tetrazol-5-ylthio, or substituted tetrazol-5-ylthio, alkynyl, alkenyl or alkyl, said alkyl or alkenyl group optionally being substituted with halo, —OR$^{10}$ or —CO$_2$R$^{10}$;

R$^3$ and R$^4$ are the same or different and each independently represents H, any of the substituents of R$^1$ and R$^2$, or R$^3$ and R$^4$ taken together represent a saturated or unsaturated C$_5$–C$_7$ fused ring to the benzene ring (Ring III);

R$^5$, R$^6$, R$^7$ and R$^8$ each independently represents H, —CF$_3$, —COR$^{10}$, alkyl or aryl, said alkyl or aryl optionally being substituted with —OR$^{10}$, —SR$^{10}$, —S(O)$_t$R$^{11}$, —NR$^{10}$COOR$^{11}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$, or R$^5$ is combined with R$^6$ to represent =O or =S and/or R$^7$ is combined with R$^8$ to represent =O or =S;

R$^{10}$ represents H, alkyl, aryl, or aralkyl;

R$^{11}$ represents alkyl or aryl;

the dotted line between carbon atoms 5 and 6 represents an optional double bond, such that when a double bond is present, A and B independently represent —R$^{10}$, halo, —OR$^{11}$, —OCO$_2$R$^{11}$ or —OC(O)R$^{10}$, and when no double bond is present between carbon atoms 5 and 6, A and B each independently represent H$_2$, —(OR$^{11}$)$_2$; H and halo, dihalo, alkyl and H, (alkyl)$_2$, —H and —OC(O)R$^{10}$, H and —OR$^{10}$, =O, aryl and H, =NOR$^{10}$ or —O—(CH$_2$)$_p$—O— wherein p is 2, 3 or 4.

2. The process according to claim 1 which comprises using a compound of formula (1.0') wherein a is N; and R$_5$, R$_6$, R$_7$, and R$_8$, are all H; and R$_1$, R$_2$, R$_3$, and R$_4$ are each independently selected from the group consisting of H or halo.

3. The process according to claim 2 which comprises using a compound of formula (1.0') wherein R$_1$ is H; and R$_2$ is Br; and R$_3$, and R$_4$, are each independently selected from the group consisting of Br and Cl.

4. The process according to claim 3 which comprises using a compound of formula (1.0') wherein X is CH.

5. The process according to claim 4 which comprises using a compound of formula (1.0') wherein R$_3$ is Br; and R$_4$ is Cl.

6. A process for producing a compound of the formula:

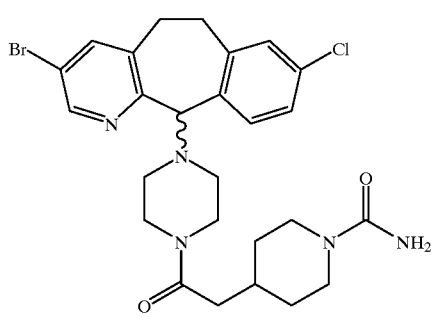
I which comprises reacting the water insoluble compound

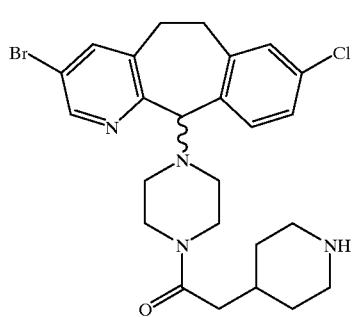

II in water with about 4 to about 10 equivalents of urea as compared to the compound of formula II, for about 3 to about 68 hours, at about 98 to about 100° C., and wherein the ratio of the compound of formula II to the water is from about 0.025 g/ml to about 0.6 g/ml.

7. The process according to claim 6, wherein the amount of urea to the amount of compound of formula II is from about 10 equivalents to about 1 equivalent of urea.

8. The process according to claim 6, wherein the reaction is run at a temperature from about 98 to about 100° C.

9. The process according to claim 6, wherein the reaction is run for about 3 to about 68 hours.

10. A process which comprises reacting a water insoluble compound of the formula

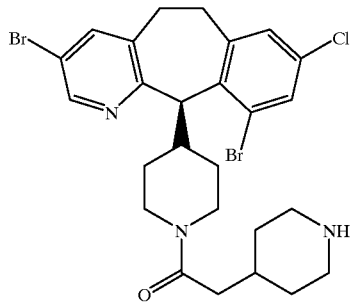

IV with an excess of urea in water to produce a compound of the formula

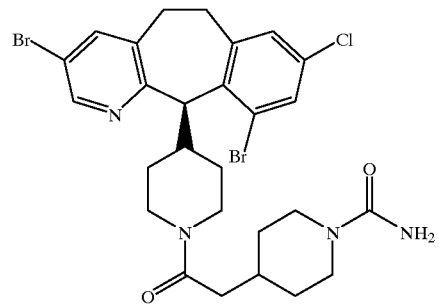

III

11. The process according to claim 1, for producing a compound of formula (1.0) which comprises reacting a compound of formula (1.0)' in water with about 4 to about 10 equivalents of urea as compared to the compound of formula (1.0)', for about 3 to about 68 hours, at about 98 to about 100° C., and wherein the ratio of the compound of formula (1.0)' to the water is from about 0.025 g/ml to about 0.6 g/ml.

12. The process according to claim 10 which comprises reacting a compound of formula (IV) in water with about 4 to about 10 equivalents of urea as compared to the compound of formula (IV), for about 3 to about 68 hours, at about 98 to about 100° C., and wherein the ratio of the compound of formula (IV) to the water is from about 0.025 g/ml to about 0.6 g/ml.

13. The process according to claim 12 wherein 10 equivalents of urea, and 1 equivalent of formula IV are used.

14. The process according to claim 12 wherein the reaction is heated at 100° C.

15. The process according to claim 12 wherein the reaction is heated at 100° C. for 68 hours.

16. The process according to claim 12 wherein 10 equivalents of urea, and 1 equivalent of formula IV are used; and the reaction is heated at 100° C. for 68 hours.

* * * * *